(12) United States Patent
Myrman

(10) Patent No.: US 6,840,239 B2
(45) Date of Patent: *Jan. 11, 2005

(54) DE-AGGREGATING AND DISPERSING DRY MEDICAMENT POWDER INTO AIR

(75) Inventor: Mattias Myrman, Stockholm (SE)

(73) Assignee: Microdrug AG, Hergiswil NW (CH)

( * ) Notice: Subject to any disclaimer, the term of this patent is extended or adjusted under 35 U.S.C. 154(b) by 261 days.

This patent is subject to a terminal disclaimer.

(21) Appl. No.: 10/134,532

(22) Filed: Apr. 30, 2002

(65) Prior Publication Data

US 2003/0192539 A1 Oct. 16, 2003

(30) Foreign Application Priority Data

Apr. 12, 2002 (SE) .............................................. 0201126

(51) Int. Cl.[7] ............................................. A61M 15/00
(52) U.S. Cl. ............................ 128/203.15; 128/203.12; 128/203.19
(58) Field of Search ................... 128/200.24, 200.12, 128/200.14, 200.21, 200.23, 203.12, 203.15, 203.19, 203.21, 204.13, 203.23, 202.21; 131/271, 273; 222/160, 161, 196; 239/690, 690.1, 697, 706; 424/45, 46, 489

(56) References Cited

U.S. PATENT DOCUMENTS

| | | | |
|---|---|---|---|
| 5,113,855 A | 5/1992 | Newhouse | |
| 5,161,524 A | 11/1992 | Evans | |
| 5,349,945 A | 9/1994 | Wass et al. | |
| 5,388,572 A | 2/1995 | Mulhauser et al. | |
| 5,388,573 A | 2/1995 | Mulhauser et al. | |
| 5,408,994 A | 4/1995 | Wass et al. | |
| 5,441,060 A | * 8/1995 | Rose et al. | ................. 131/271 |
| 5,469,843 A | 11/1995 | Hodson | |
| 5,655,523 A | 8/1997 | Hodson et al. | |
| 5,694,920 A | 12/1997 | Abrams et al. | |
| 6,074,688 A | * 6/2000 | Pletcher et al. | ............ 427/2.14 |
| 2003/0192540 A1 | * 10/2003 | Myrman et al. | ....... 128/203.15 |

FOREIGN PATENT DOCUMENTS

| | | |
|---|---|---|
| EP | 0 069 715 A1 | 1/1983 |
| EP | 0 414 536 A2 | 2/1991 |
| WO | 02/18000 A1 | 3/1992 |
| WO | 01/34233 A1 | 5/2001 |
| WO | 02/24264 A1 | 3/2002 |

* cited by examiner

Primary Examiner—Henry Bennett
Assistant Examiner—Teena Mitchell
(74) Attorney, Agent, or Firm—Young & Thompson

(57) ABSTRACT

A method based on an Air-razor tool is disclosed thereby providing de-aggregation and dispersal into air of a dose of finely divided medication powder. In sucking air through a nozzle, particles of a powder dose made available to the nozzle, are gradually de-aggregated and dispersed into a stream of air entering the nozzle. The gradual de-aggregation or dispersal is produced by a relative motion introduced between the nozzle and the dose. In a preferred embodiment, the powder is deposited onto a substrate, occupying a larger area than the area of the nozzle inlet. The nozzle is preferably positioned outside the powder area, not accessing the powder in its relative motion until a created air stream entering the nozzle, exceeds a threshold flow velocity.

26 Claims, 23 Drawing Sheets

Fig. 29

```
┌─────────────────────────────┐
│ Position nozzle with inlet  │
│    adjacent to dose area    │
└─────────────────────────────┘
              ↓
┌─────────────────────────────┐
│ Apply a suction effort to the│
│ nozzle outlet, thus creating │
│ an air stream into the nozzle│
└─────────────────────────────┘
              ↓
┌─────────────────────────────────┐
│ Move the nozzle relative to the │
│ dose to produce a powder Air-razor│
│ effect on the particles of the dose│
└─────────────────────────────────┘
              ↓
┌─────────────────────────────────┐
│ De-aggregate and disperse into air│
│ particles in the dose gradually using│
│         the Air razor           │
└─────────────────────────────────┘
              ↓
┌─────────────────────────────────┐
│ Let the air stream access and   │
│ disperse into air particles of the dose│
│ gradually by arranging traversing of│
│   the dose area by the nozzle   │
└─────────────────────────────────┘
```

Fig. 30

DE-AGGREGATING AND DISPERSING DRY MEDICAMENT POWDER INTO AIR

TECHNICAL FIELD

The present invention relates to a method for de-aggregating and dispersing into air a metered dose of dry medication powder from a substrate member and more specifically a method of delivering a metered dose continuously to a user inhaling through a dry powder inhaler device.

BACKGROUND

The dosing of drugs is carried out in a number of different ways in the medical service today. Within health-care, there is a rapidly growing interest in administering locally or systemically acting medication in prescribed doses of powder directly to the airways and lungs of a patient by means of an inhaler in order to obtain an effective, quick and user-friendly administration of such drugs.

A dry powder inhaler, DPI, represents a device intended for administration of doses of powder into the deep and/or upper lung airways by oral inhalation. However, deep lung deposition of medicament is a more difficult proposition and has only recently come into focus. Most inhalers on the market today are designed for treatment of ailments in the airways or local lung, like asthma, where the objective often is local, not deep lung, deposition. When the objective is a systemic delivery of the medication, then a deep lung deposition of the powder is preferred and usually necessary for maximum efficiency. The deep lung is defined as the peripheral lung and alveoli, where direct transport of a substance to the blood can take place. If a particle is to reach into the deep lung the aerodynamic particle size should typically be less than 3 $\mu$m, and for a local lung deposition, typically about 5 $\mu$m. Larger particle sizes will easily stick in the mouth and throat. Thus, regardless of whether the objective is a local or systemic delivery of a drug, it is important to keep the particle size distribution of the dose within tight limits to ensure that a high percentage of the dose is actually deposited where it will be most effective.

Particle size is especially important for a successful delivery to the deep lung upon inhalation. Furthermore, for optimal results, the inspiration must take place in a calm manner to decrease air speed and thereby reduce deposition by impaction in the upper respiratory tracts. The advantages of using the inhalation power of the user to full potential in a prolonged, continuous dose delivery interval within the inhalation cycle is disclosed in our Swedish Patent no. SE 9904081-8 (WO 01/34233 A1), which is hereby incorporated herein by reference. The patent presents several devices for efficient distribution of pharmaceutical compositions in fine powder form in the inspiration air, without using other sources of energy than the power of the air in the user's inhalation.

Powders for inhalation have a tendency of aggregating, in other words to clod or to form smaller or larger lumps of particles, which then have to be de-aggregated before the particles enter into the mouth of the user. De-aggregating is defined as breaking up aggregated powder by introducing energy; e.g. electrical, mechanical, pneumatic or aerodynamic energy. To succeed with systemic delivery of medication powders by inhalation to the deep lung, it is important to achieve a high degree of de-aggregation of the medication powder in the inhaled air. In most cases, treatment of a patient is not a single occurrence, but has to be repeated and in some chronic cases, treatment has to be on a continuous basis. In all cases, de-aggregation must be very repeatable and dosing must be kept within tight tolerances from one administration to the next.

A majority of dry powder inhalers of today presents rather moderate deaggregation capacity. Current inhalation devices intended for asthma and other lung diseases normally deliver the dispensed drug particles in a larger size range than optimal for deep lung deposition. This is often caused by inadequate de-aggregation of powder particle aggregates with a primary particle size in the range 2–3 $\mu$m. Thus, the inhaled dose consists of aggregates of smaller particles. This entails several disadvantages:

The uniformity of aerodynamic particle size distribution between different doses may vary considerably, because the de-aggregation is sensitive to slight difference in inspiration conditions from one inhalation to the next.

Particle size distribution of the delivered dose may have a tail of big aggregates, which will deposit in the mouth and upper airways.

Retention of the substance in the inhaler may vary with the aerodynamic particle size distribution and may hence be difficult to predict.

Thus, for a consistent, predictable and repeatable delivery of medicaments to the lungs there is a need of a de-aggregating method capable of producing reproducibly a very high degree of de-aggregation of the dry powder medicament. This is especially true for systemically acting drugs, where a deep lung deposition is normally required. In addition, for locally acting medicaments, where usually a local lung deposition is preferred, a high degree of de-aggregation of the medication powder is an advantage. Preferably, the de-aggregating method ought to be insensitive as far as possible to the inhalation effort produced by the user, such that the delivered aerodynamic particle size distribution in the inhaled air is independent of the inhalation effort. The average aerodynamic particle size, which influences the deposition pattern in the lungs, can be controlled by controlling the primary particle size distribution of the particles constituting the powder.

Introducing special devices as for example spacers and/or external sources of energy to amplify the inhalation energy provided by the user during the act of inhalation are common methods in prior art inhalers for improving the performance in terms of de-aggregation and dosing predictability and repeatability. The addition of external sources of energy leads to more complex and expensive inhalers than necessary, besides increasing the demands put on the user in maintaining the inhaler.

Over the years, many methods and devices have been tried in order to improve the performance of drug delivery systems based on inhalation. For instance, U.S. Pat. No. 480,505, dated as early as Aug. 9, 1892, describes a nasal respirator device, including reticulated material and adapted to receiving a porous medium impregnated with medicine. Nets, screens or membranes with interstices are well known to a person skilled in the art, as components in many inhaler designs, either as carriers of drugs or elements to facilitate the release of the dose to a user. An example of a prior art inhaler device using a perforated membrane as a dispensing element for an active compound of medicament is disclosed in a European patent EP 0 069 715 B1 with priority date Aug. 7, 1981. The patent teaches an inhaler comprising a nozzle, an air conduit and a displaceable dispensing element in the form of a perforated membrane, for dispensing the medicament from a storage chamber into the air conduit. Dry powder inhaler medicament carriers with interstices for enhancement of de-aggregation of a powder dose are dealt with in several later documents e.g. U.S. Pat. Nos. 5,388, 572; 5,388,573; 5,460,173; 5,647,347; 5,823,182; 6,245,339 B1 and WIPO publication Nos. WO94/20164; WO98/ 04308. The carriers and methods, taught in the referred documents, are characterized in that the powdered medicament is impregnated or embedded in and across interstices at spaced locations in the carrier, thus forming one or more doses of medicament. A dose is then put in a flow channel connected to a mouthpiece. As the user inhales through the mouthpiece the created air stream forces the aggregated dry powder particles of the dose loaded onto or into the carrier to be released into air and de-aggregated by the shearing force of the air as it passes through the interstices and past the aggregated powder particles. Thus, a main purpose of the net or screen type of carrier presented in the referred documents is to facilitate de-aggregation of the dose. However, examples in some of the documents show pressure chambers or similar means for creating a high-pressure air pulse, 70 psig (=490 kPa) in one case, necessary to blow the dose off the carrier. A pressure of 70 psig is about 100 times higher than the pressure drop produced by the inhalation of a user. A normal inspiration by an adult produces about 5 kPa and an external energy source is therefore necessary in order to produce the air pulse. The suggested methods seem to be limited in terms of dose mass, only being suitable for rather small doses. The teachings also suggest using ordered mixtures of active substance and some excipient, to further improve de-aggregation, which further limits the active medicament mass in the dose.

Another example of an inhalation device addressing the problem of de-aggregation is disclosed in U.S. Pat. No. 5,694,920 and further improvements of the inhaler are disclosed in U.S. Pat. Nos. 6,026,809 and 6,142,146. The inventions teach that de-aggregation of a medication powder may be provided by a vibrator, which directly or indirectly imparts mechanical energy of suitable frequency and power to the powder. The powder is thus fluidized and de-aggregated. Particles of a size suitable for inhalation are then lifted out from the fluidized powder and introduced in an air stream by an electric field of suitable strength established across the air stream. The particles are then delivered to a user by the air stream. Clearly, it is necessary to provide external power in electro-mechanical form to achieve de-aggregation, which still seems to be only partially successful.

Prior art methods and devices leave much to be desired when it comes to dose conformity, particle de-aggregation and efficient administration of the medication substance. Furthermore, prior art methods of de-aggregating and dispersing into air a dose seem to require high levels of de-aggregating energy, which lead to more or less complicated inhaler designs. Furthermore, achieving an objective of efficient de-aggregation in terms of percentage mass of particles less than 5 μm dispersed into air relative to available powder mass seems to be a far way off. Till the present day too little has been done to develop user friendly, highly efficient methods and devices for de-aggregating and dispersing into air a quantity of medication powder, especially when using the effort of the user's inhalation as the single source of energy.

SUMMARY

A method for de-aggregating and dispersing into air a dose of finely divided medication powder and more specifically a method of administering the dose to a user are disclosed. In contrast to prior art, the present invention does not require other sources of energy besides the power of the inhalation effort by the user to produce a very high degree of de-aggregation and efficient dispersal into air of a dry powder dose.

A powder Air-razor method is disclosed, providing de-aggregation and dispersal into air of a dose of finely divided medication powder. Utilizing an effort of sucking air through a nozzle, the particles in the powder dose, made available to the nozzle, are gradually de-aggregated and dispersed into a stream of air entering the nozzle. The gradual de-aggregation and dispersal will be produced by a relative motion introduced between the nozzle and the dose. In a preferred embodiment, the powder is deposited onto a substrate, the accumulated powder occupying a larger area than the area of the nozzle inlet. The nozzle is preferably positioned outside the powder area, not accessing the powder by the relative motion until the air stream into the nozzle, created by the suction, has passed a threshold flow velocity. Coincidental with the application of the suction, or shortly afterwards the relative motion will begin such that the nozzle traverses the powder dose gradually. The high velocity air going into the nozzle inlet provides plenty of shearing stress and inertia energy as the flowing air hits the leading point of the border of the dose contour. This powder Air-razor method, created by the shearing stress and inertia of the air stream, is so powerful that the particles in the particle aggregates in the powder adjacent to the inlet of the moving nozzle are released, de-aggregated to a very high degree as well as dispersed and subsequently entrained in the created air stream going through the nozzle.

A powder Air-razor method for de-aggregating and dispersing a metered dose according to the present invention is set forth herein, and a method of administering a metered dose to a user is also set forth herein.

SHORT DESCRIPTION OF THE DRAWINGS

The invention, together with further objects and advantages thereof, may best be understood by referring to the following detailed description taken together with the accompanying drawings, in which:

Figure 29:
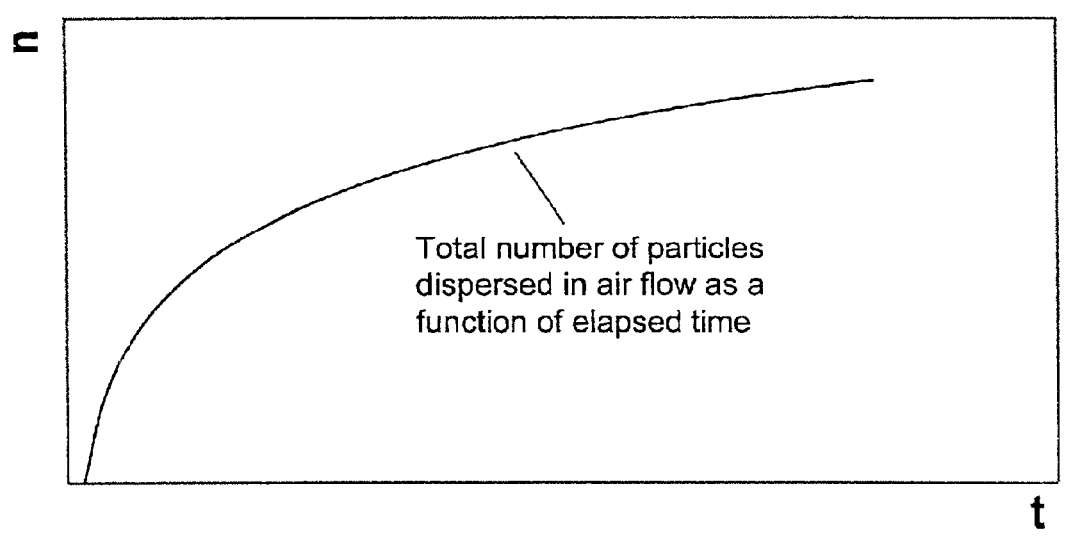

FIG. 29 illustrates the number of particles released into air as a function of time, and FIG. 30 illustrates in a flow chart diagram the main steps of the method according to the present invention.

DESCRIPTION

The present invention discloses a powder Air-razor method of de-aggregating and dispersing into air a metered dose of dry medication powder being deposited onto a substrate member, which is part of a dosing member supporting at least one dose. The invention teaches that a dose of finely divided dry medication powder may be delivered to a user with an extremely high degree of de-aggregation of the powder.

An important element of the Air-razor method is a relative motion between a nozzle and a powder dose. In the document the term "relative motion" refers to the non-airborne powder in more or less aggregated form, which constitutes a dose, being gradually moved, relatively speaking, by the motion into close proximity to said nozzle, where de-aggregation and dispersal into air of individual powder particles may take place. Said term does not refer to airborne powder particles already entrained in air. Therefore, the mentioning of "motion" or "moving" in relation to "powder" or "powder dose" or "dose" refers to the contour of the dose before the powder particles are released and dispersed into air.

The medication powder comprises at least one pharmacologically active substance and optionally one or more excipients. In the document the terms "powder" or "medication powder" are used to signify the substance in the form of dry powder, which is the subject of de-aggregation and dispersal into air by the disclosed invention and intended for deposition at a selected target area of a user's airways. Optional excipients may or may not de-aggregate in a similar way as the active pharmacological substance, depending on the design of the powder. For example, an ordered mixture comprises an excipient characterized by particles considerably larger than those of the pharmacologically active substance.

Figure 1:
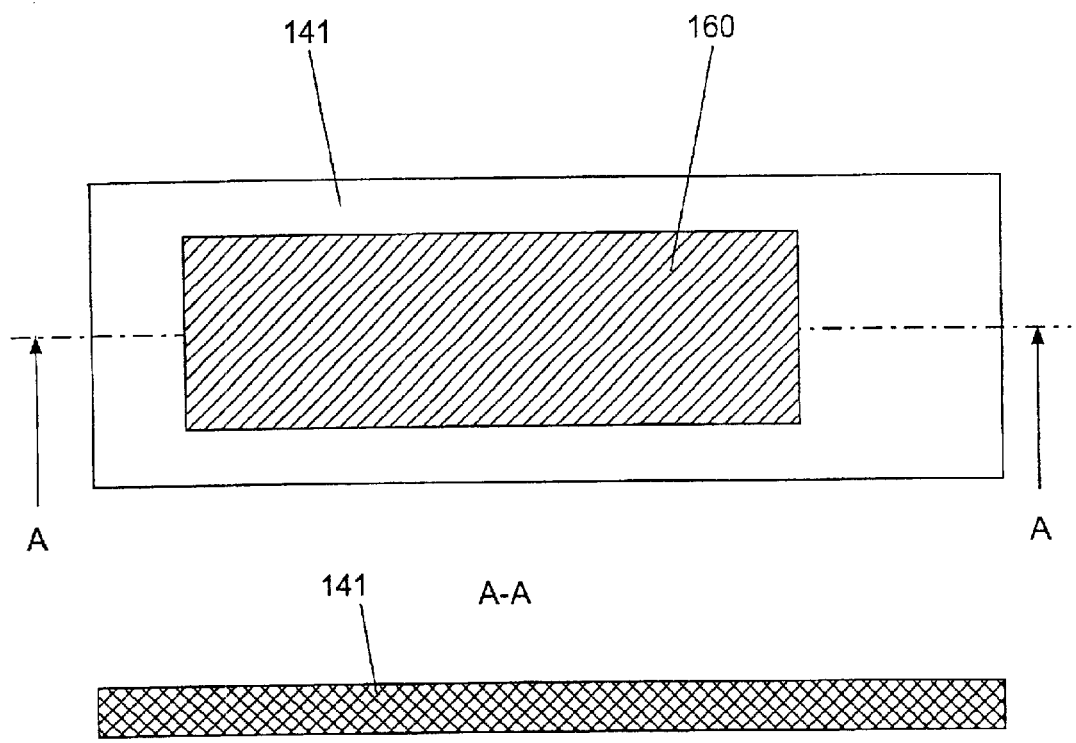
FIG. 1 illustrates in top and side views a first embodiment of a non-porous, non-perforated substrate member.
Figure 2:
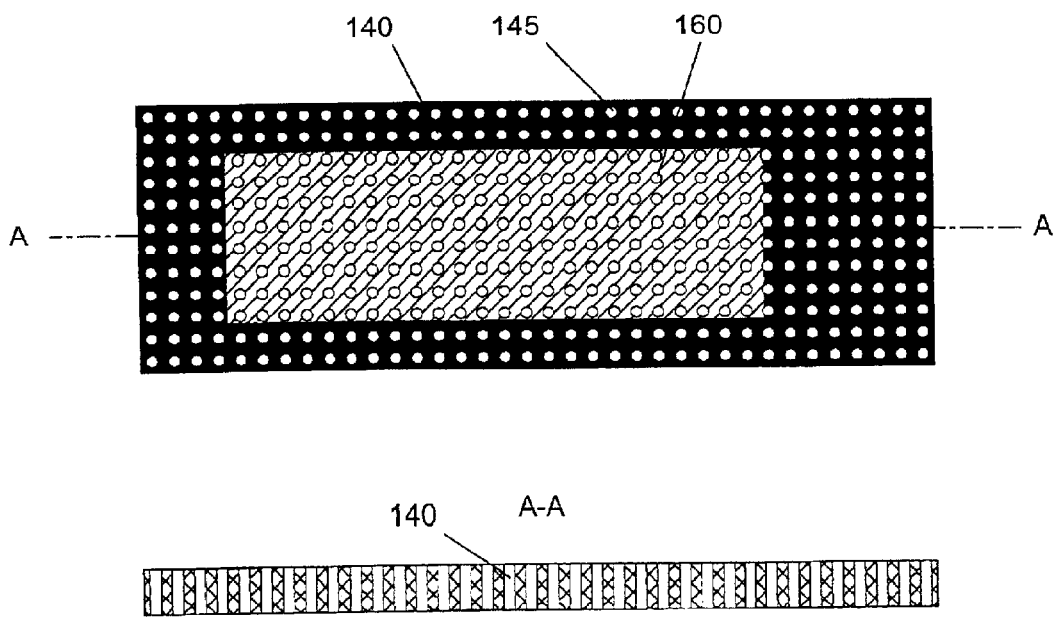
FIG. 2 illustrates in top and side views a first embodiment of a perforated substrate member.
Figure 3:
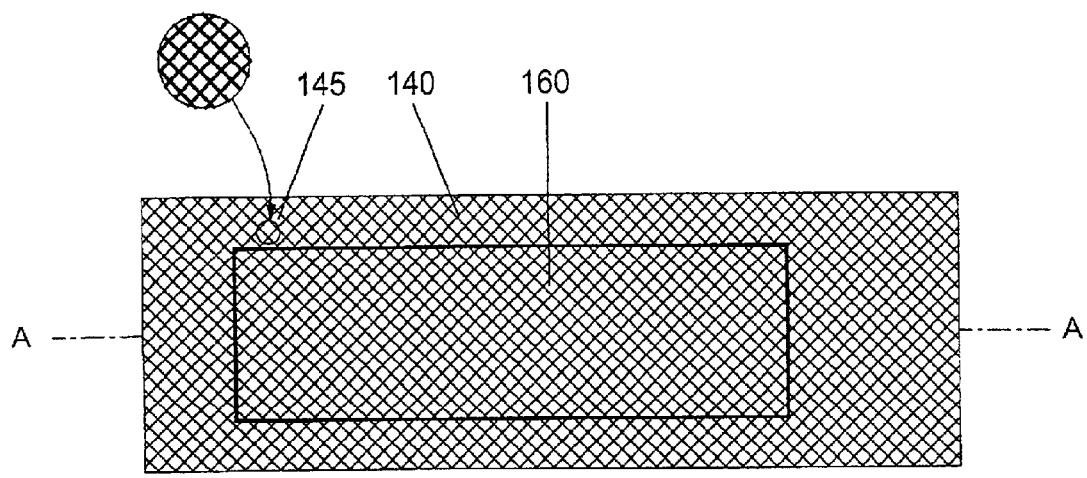
FIG. 3 illustrates in top and side views a first embodiment of a porous substrate member.
Figure 3:
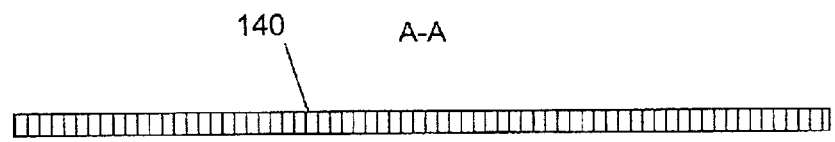
Figure 4:
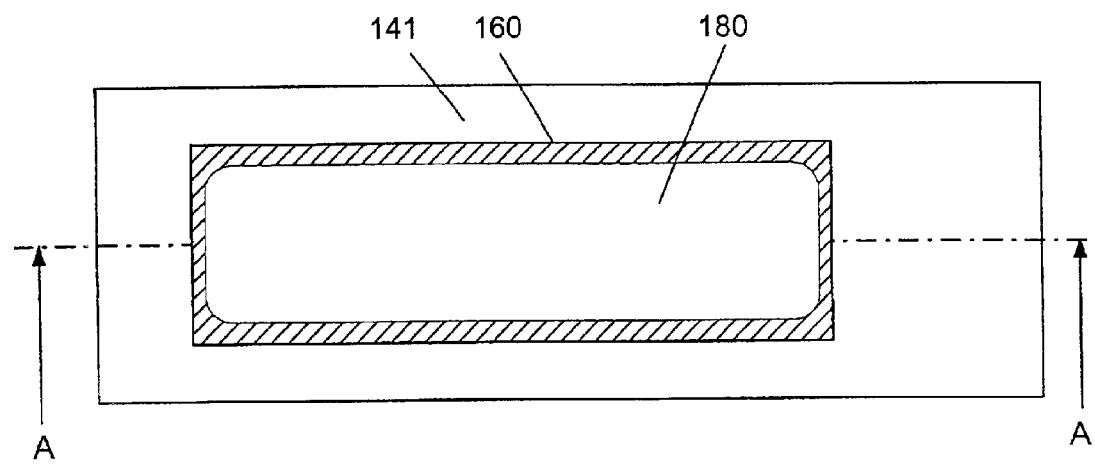
FIG. 4 illustrates in top and side views a metered dose formed as a strip on a target area of a non-perforated substrate member.
Figure 4:
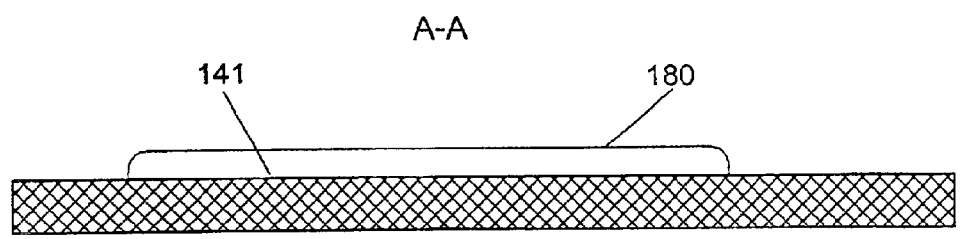
Figure 5:
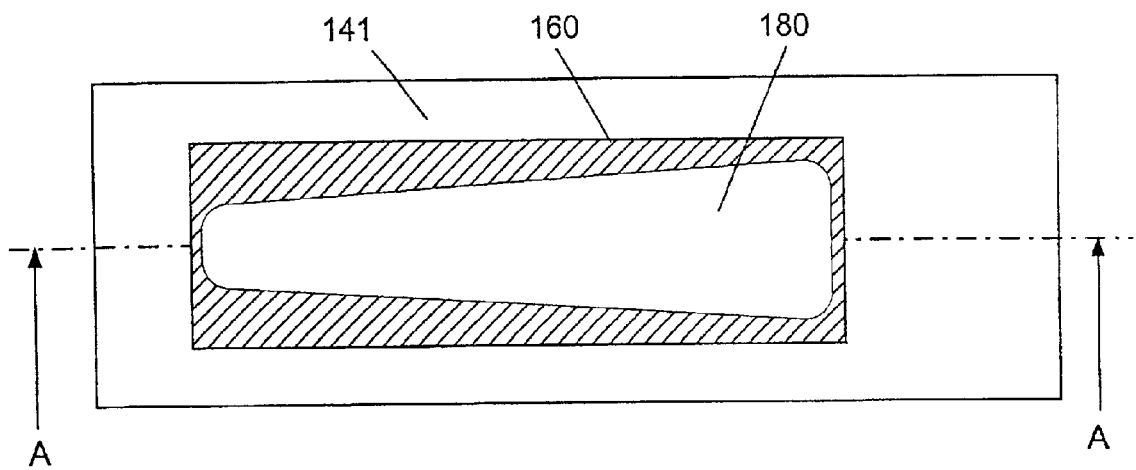
FIG. 5 illustrates in top and side views another metered dose formed as a strip on a target area of a non-perforated substrate member.
Figure 5:
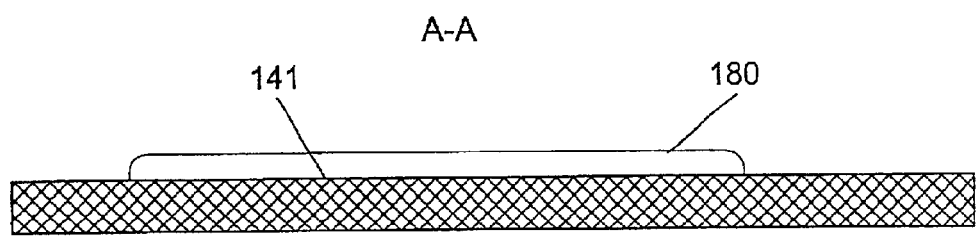
Figure 6:
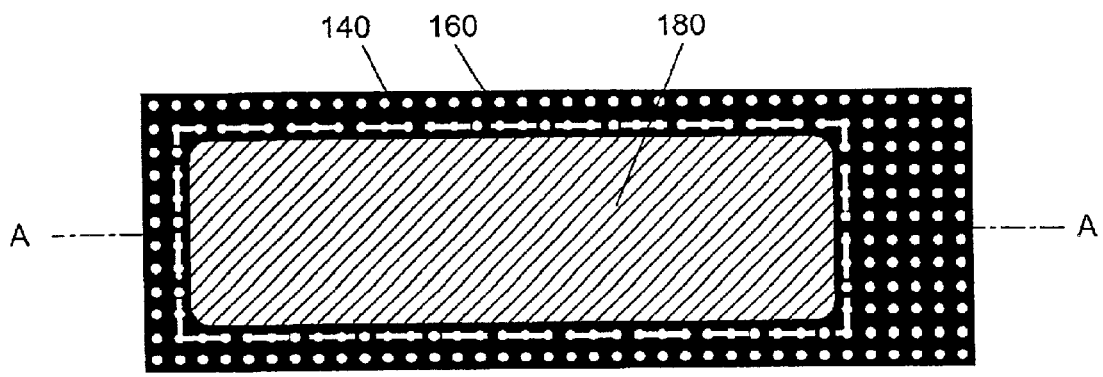
FIG. 6 illustrates in top and side views a metered dose formed as a strip on a target area of a perforated substrate member.
Figure 6:
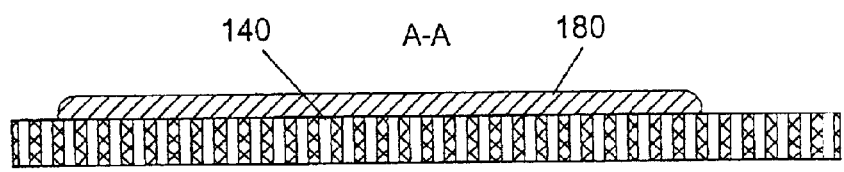
Figure 7:
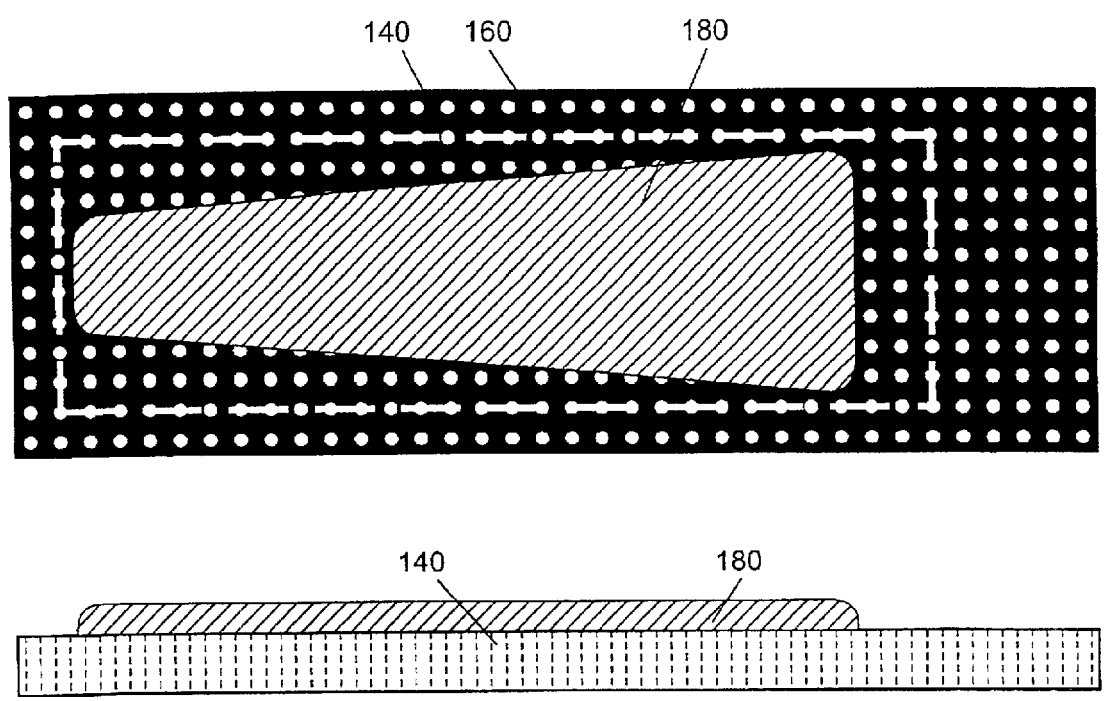
FIG. 7 illustrates in top and side views another metered dose formed as a strip on a target area of a perforated substrate member.
Figure 8:
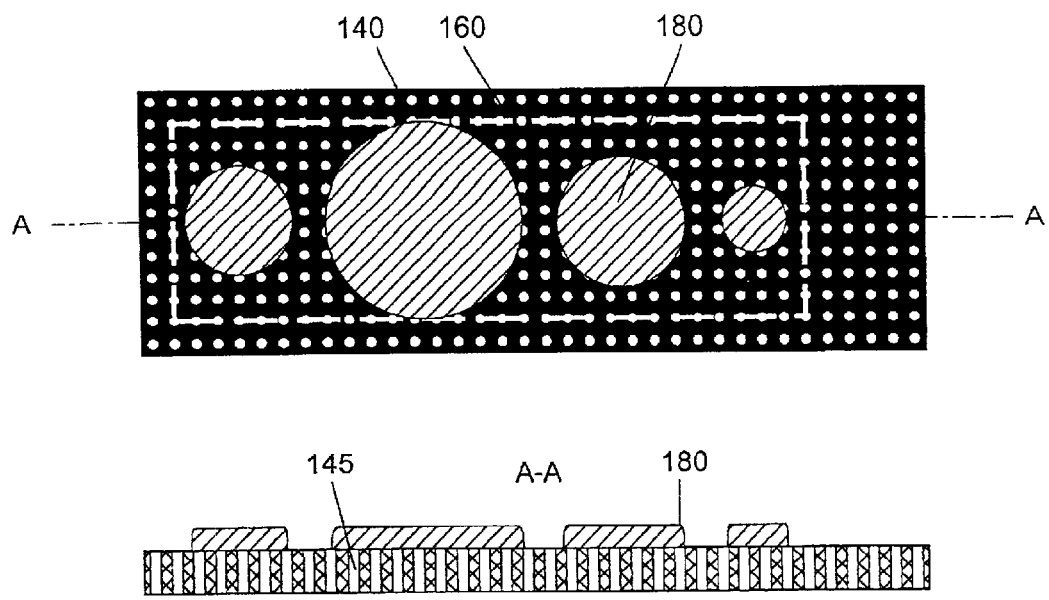
FIG. 8 illustrates in top and side views another metered dose formed as a string of dots onto a target area of a perforated substrate member.
Figure 9:
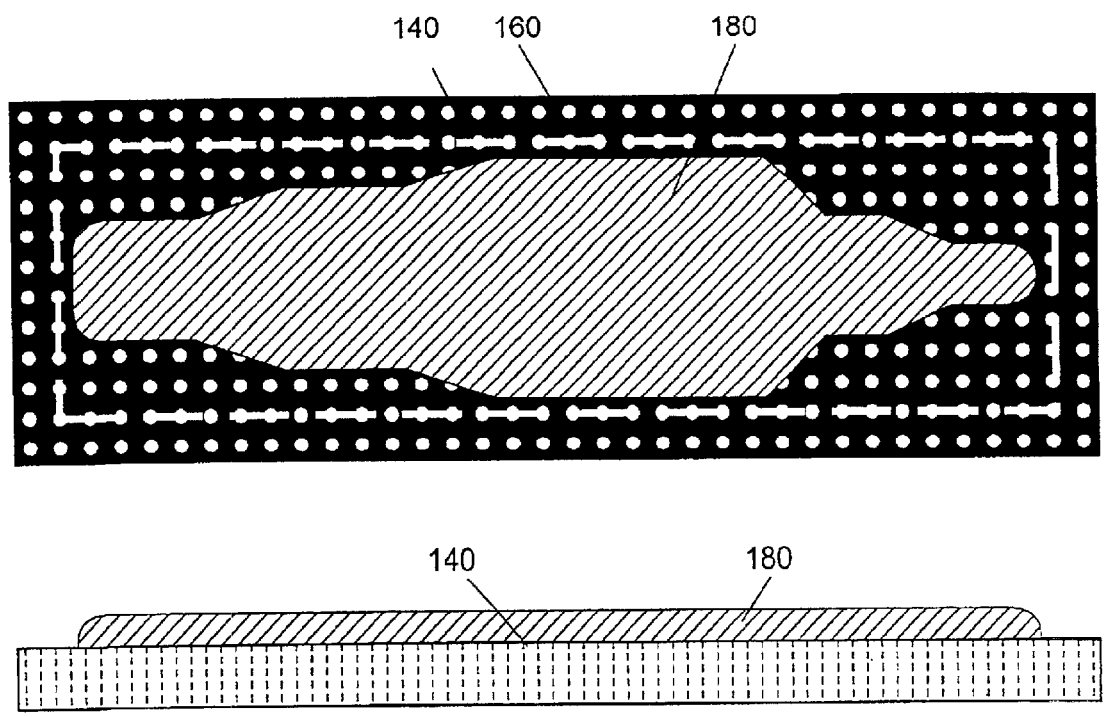
FIG. 9 illustrates in top and side views another metered dose formed as a strip on a target area of a perforated substrate member.
Figure 10:
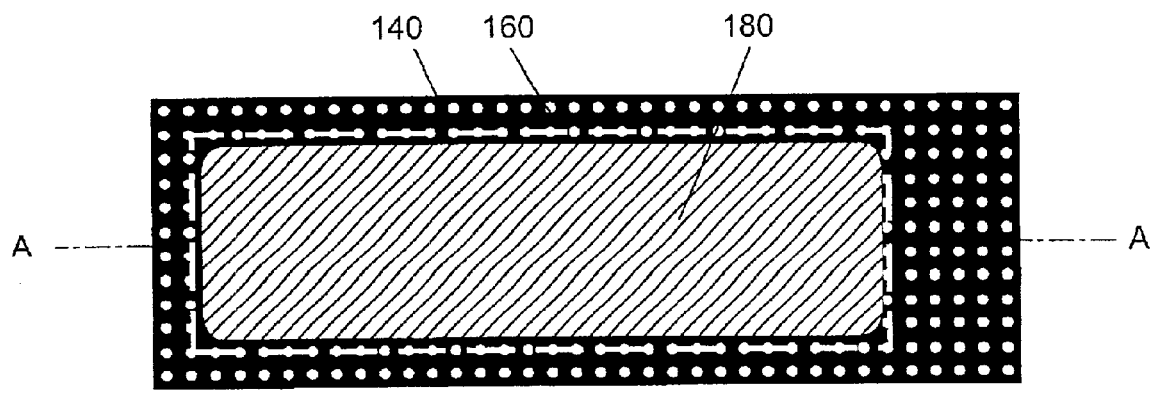
FIG. 10 illustrates in top and side views another metered dose formed as a strip on a target area of a perforated substrate member.
Figure 10:
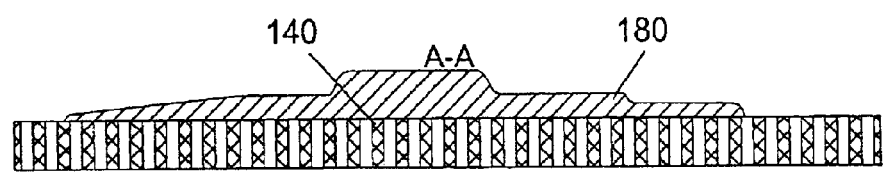
Figure 11:
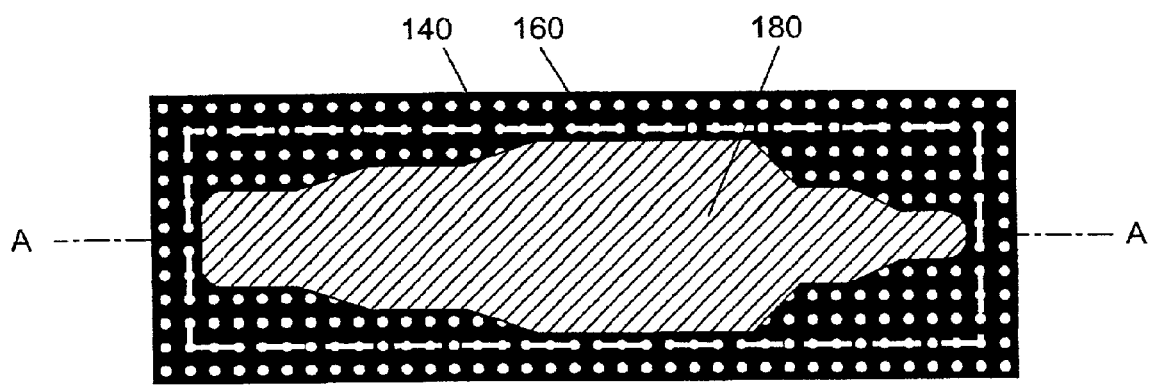
FIG. 11 illustrates in top and side views another metered dose formed as a strip on a target area of a perforated substrate member.
Figure 11:
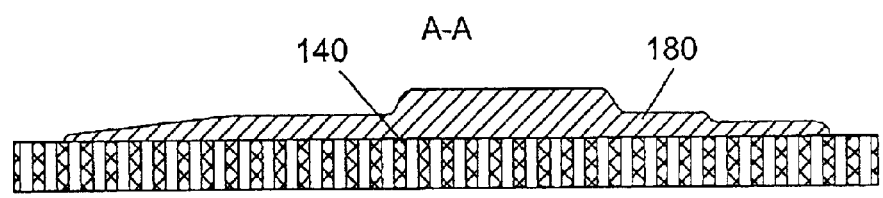
Figure 12:
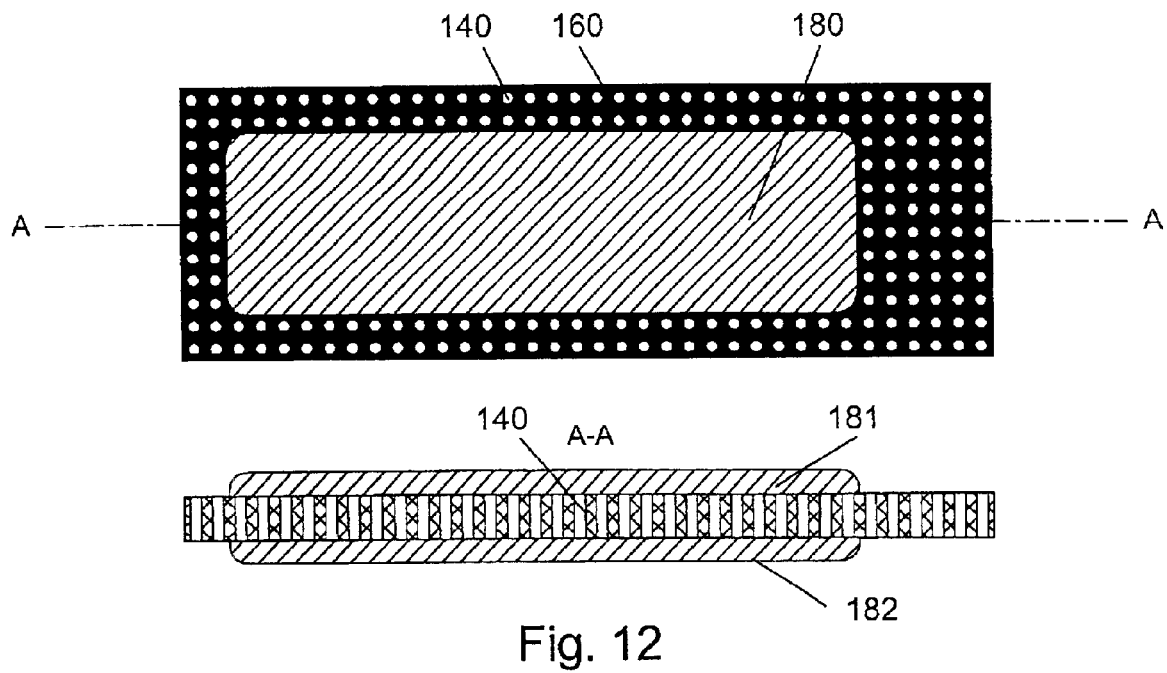
FIG. 12 illustrates in top and side views a metered dose formed as two part-doses on a target area, one on each side of a perforated substrate member.
Figure 13:
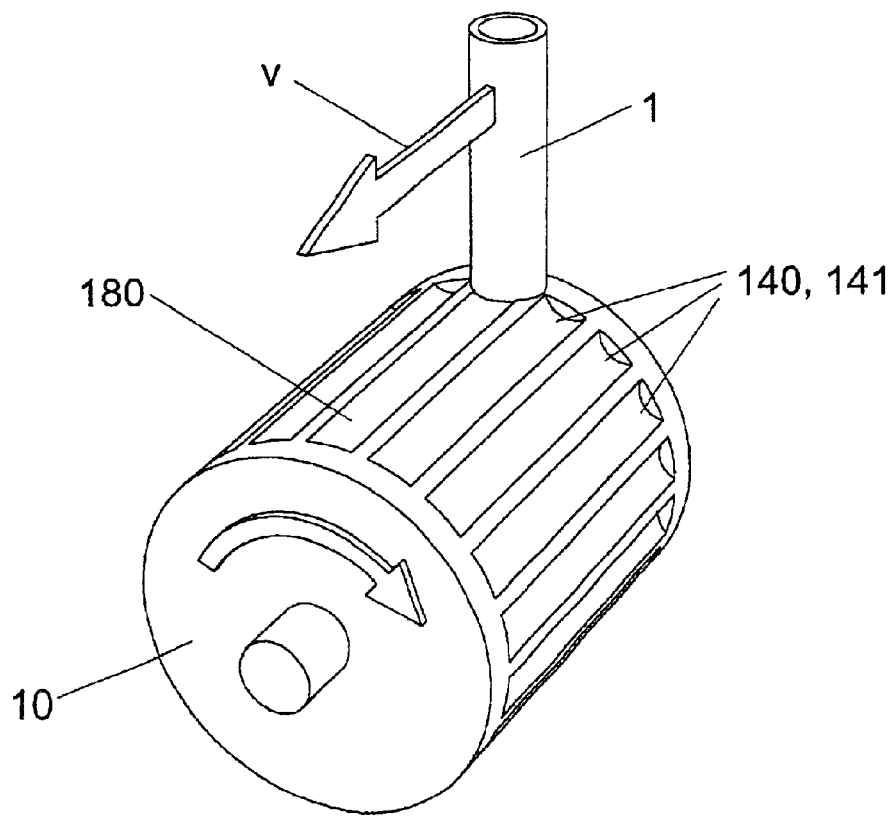
FIG. 13 illustrates a dosing member in the shape of a cylinder with longitudinally arranged multiple dose bed elements.
Figure 14:
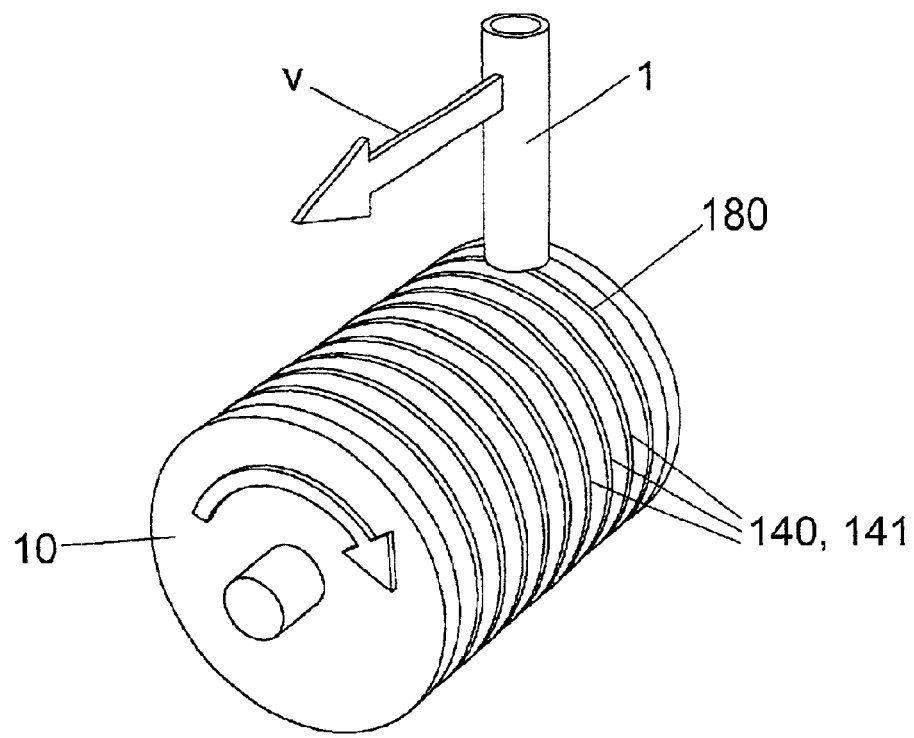
FIG. 14 illustrates a dosing member in the shape of a cylinder with circularly arranged multiple dose bed elements.
Figure 15:
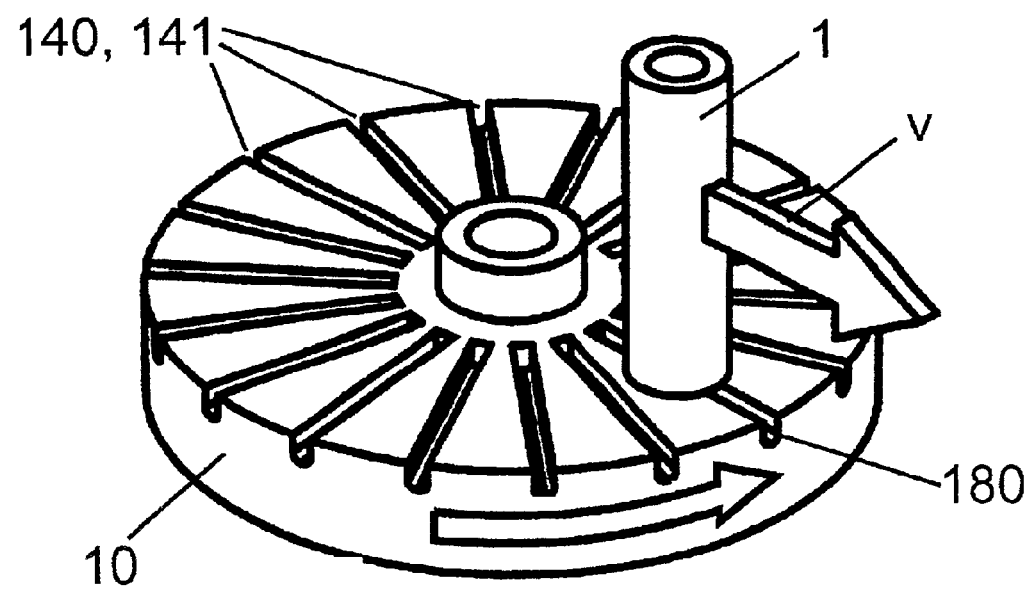
FIG. 15 illustrates a dosing member in the shape of a disc with radially arranged multiple dose bed elements.
Figure 16:
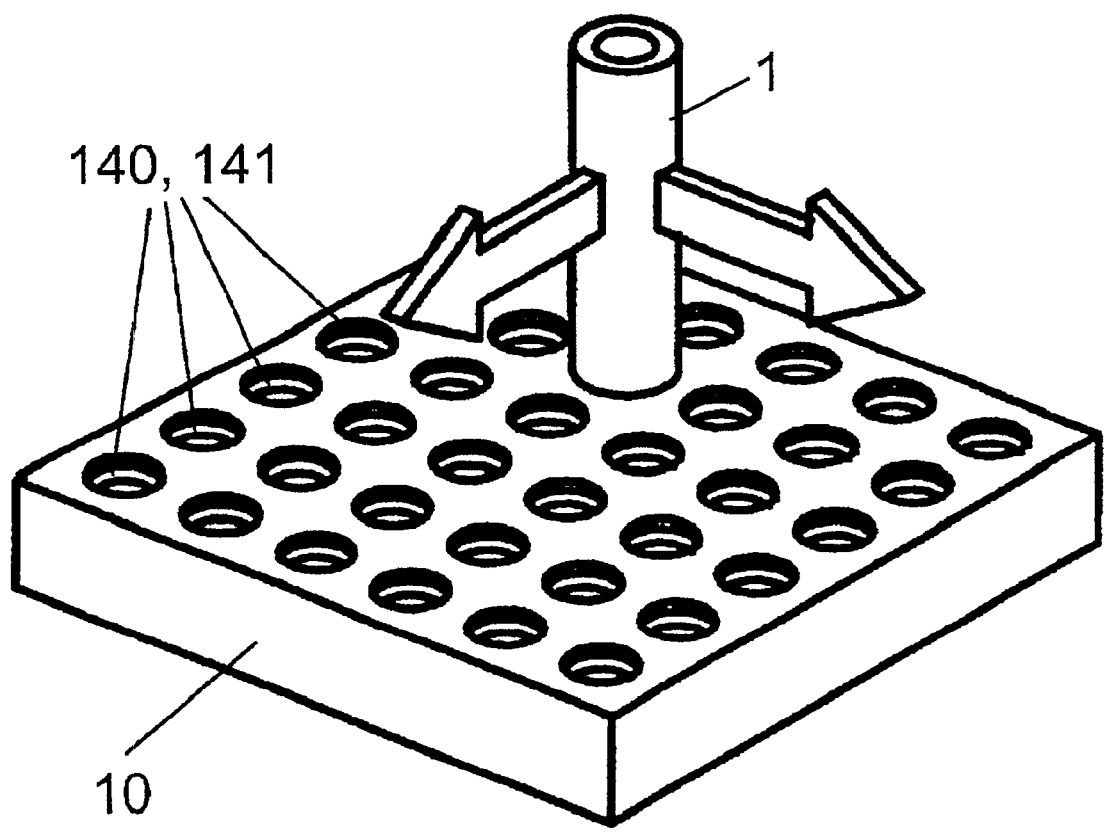
FIG. 16 illustrates a dosing member in the shape of a sheet with circular multiple dose bed elements.

Referring to FIGS. 1–30 of the drawings wherein like numerals indicate like elements throughout the several views, three different embodiments of a substrate member are illustrated in FIGS. 1–3 here offered as examples. FIG. 1 illustrates a non-porous, non-perforated substrate member 141, while FIG. 2 illustrates a perforated substrate member 140 and FIG. 3 illustrates a porous substrate member, also designated 140. The characteristic difference between a perforated or porous substrate member 140 on the one hand and a non-porous or non-perforated one 141 on the other, is that the former lets air through the substrate including the reserved dose target area 160, while the latter does not let air through. Different physical configurations of a deposited dose onto examples of substrate members 140 and 141 are illustrated in FIGS. 4–12, all of which illustrate an elongated dose strip except FIG. 8, which illustrates a dose formed as a series of consecutive spots of equal or varying sizes. The dose bed element 140, 141 may be folded if necessary e.g. in order to put a large dose area into a small allotted space of the dosing member. Different types of dosing members 10 are disclosed in FIGS. 13–16.

Figure 17A:
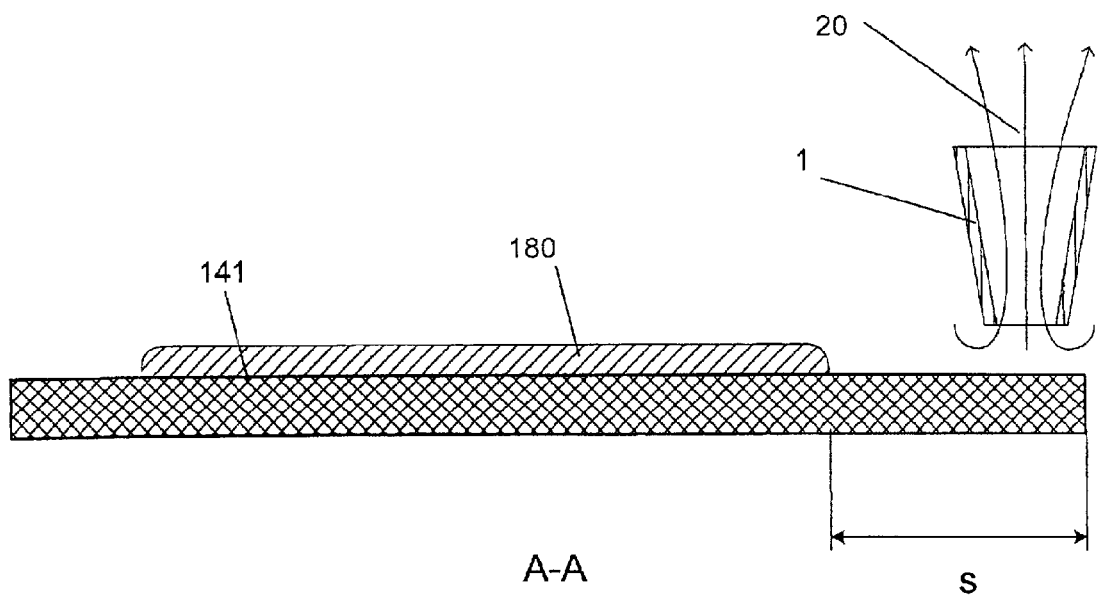
FIG. 17a illustrates in a sectional view an example of a dose on the surface of a non-perforated substrate member and adjacent to the same side as the dose, a nozzle in the starting position before the dose is released.
Figure 17B:
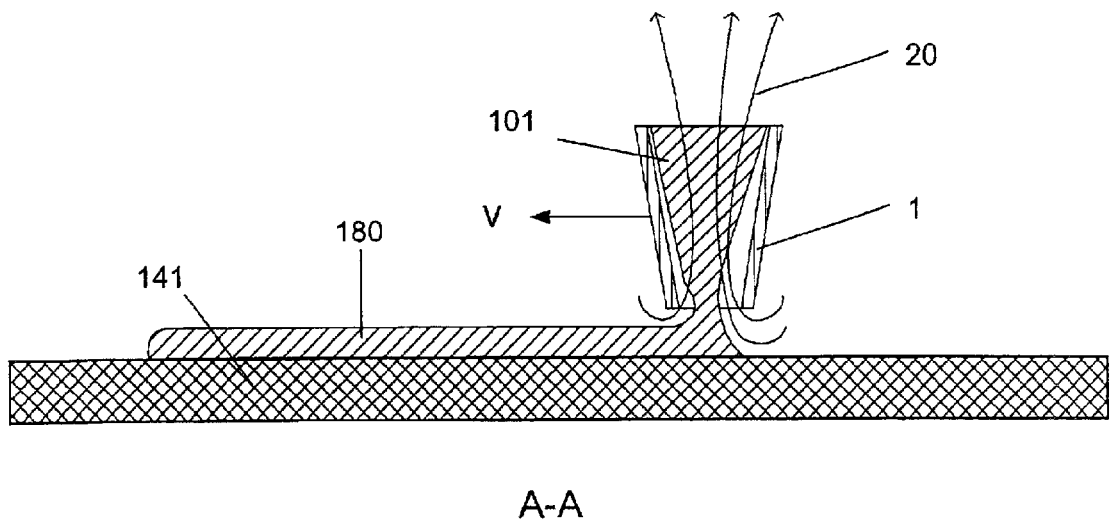
FIG. 17b illustrates in a sectional view an example of a dose on the surface of a non-perforated substrate member and adjacent to the same side as the dose, a moving nozzle sucking up the powder particles dispersed into the air stream.

A preferred embodiment of the invention is illustrated in FIG. 17a, showing in a sectional view A—A an example of a medication powder 180 deposited onto the surface of a non-perforated, non-porous substrate member 141 and on the same side of the substrate member as the powder, a nozzle 1 in a starting position before the powder is released. FIG. 17b illustrates the powder Air-razor method by showing the nozzle moving in relation to the substrate member, and showing how the powder 180 is being released, de-aggregated and dispersed into air 20 from the surface of the substrate member 141 by a stream of air hitting the powder before the air stream goes into the inlet aperture of the moving nozzle.

Figure 18A:
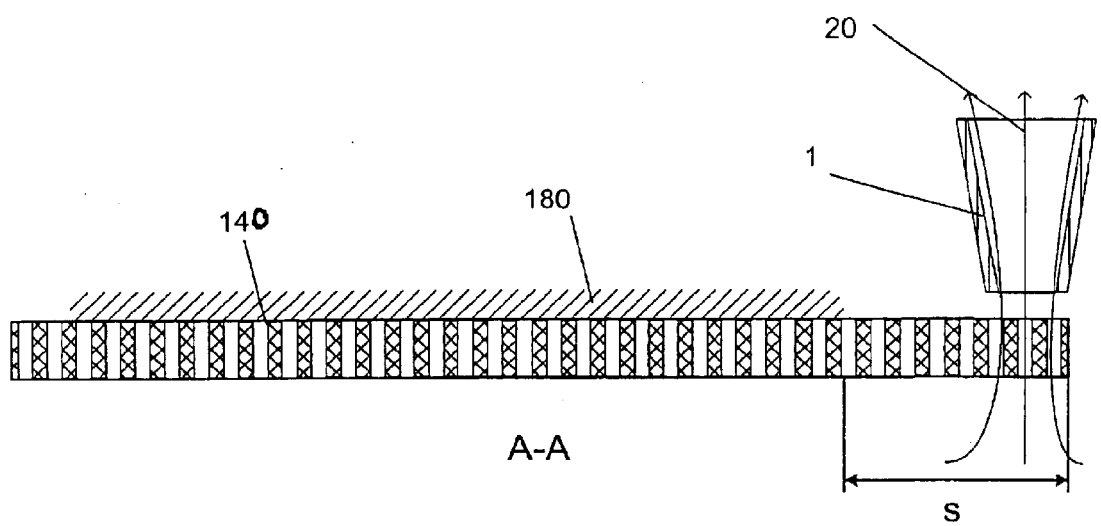
FIG. 18a illustrates in a sectional view an example of a dose on the surface of a perforated substrate member and on the same side as the dose, a nozzle in a starting position before the dose is released.
Figure 18B:
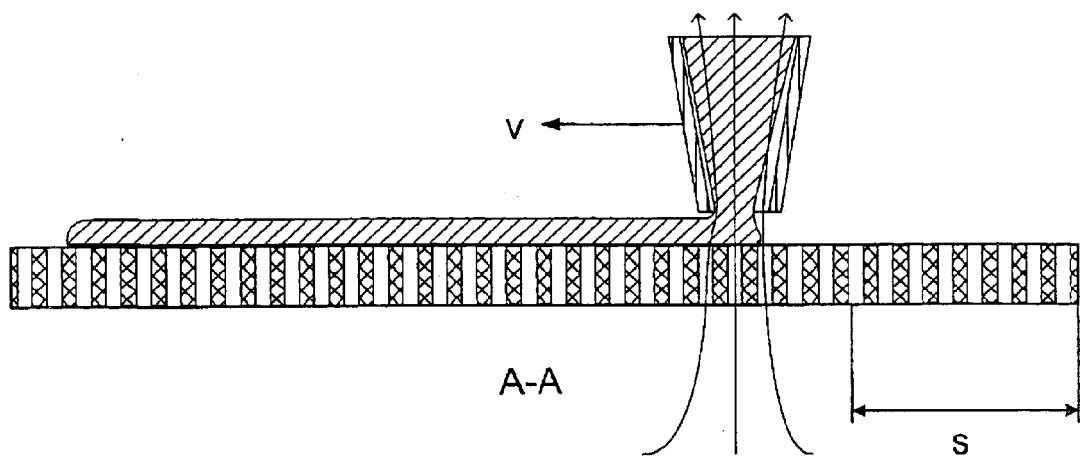
FIG. 18b illustrates in a sectional view an example of a dose on the surface of a perforated substrate member and adjacent to the same side as the dose, a moving nozzle sucking up the powder particles dispersed into the air stream.

Another embodiment is illustrated in FIG. 18a, showing in a sectional view A—A an example of a medication powder 180 deposited onto the surface of a perforated substrate member 140 and on the same side of the substrate member as the powder, a nozzle 1 in a starting position before the powder is released. FIG. 18b illustrates the powder Air-razor method by showing the nozzle moving relative to the substrate, and showing how the powder is being released, de-aggregated and dispersed into air 20 from the surface of the substrate member 140 by a stream of air, which at least in part goes through the perforations first, then through the powder and into the moving nozzle.

Figure 19A:
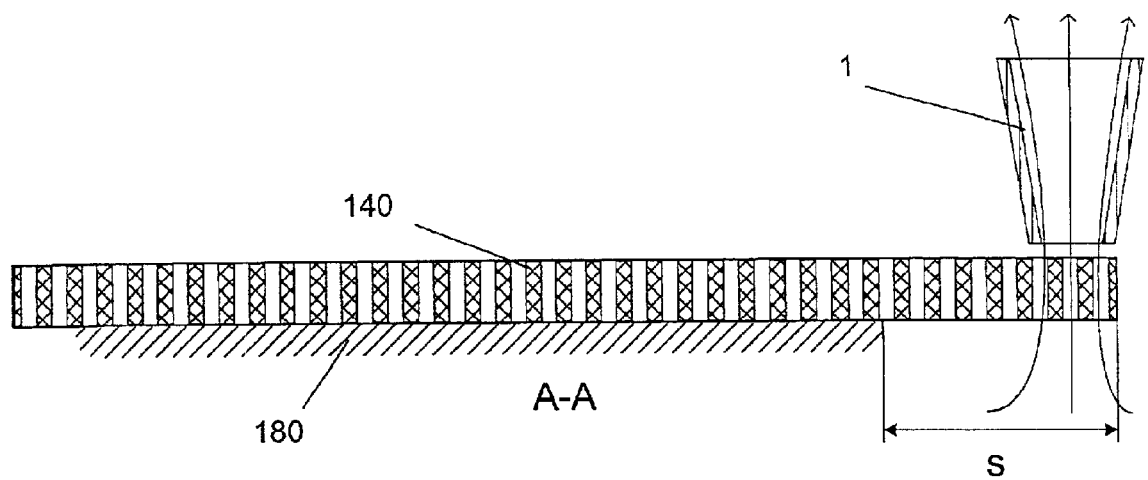
FIG. 19a illustrates in a sectional view an example of a dose on the surface of a perforated substrate member and a nozzle adjacent to the other side of the substrate member in a starting position before the dose is released.
Figure 19B:
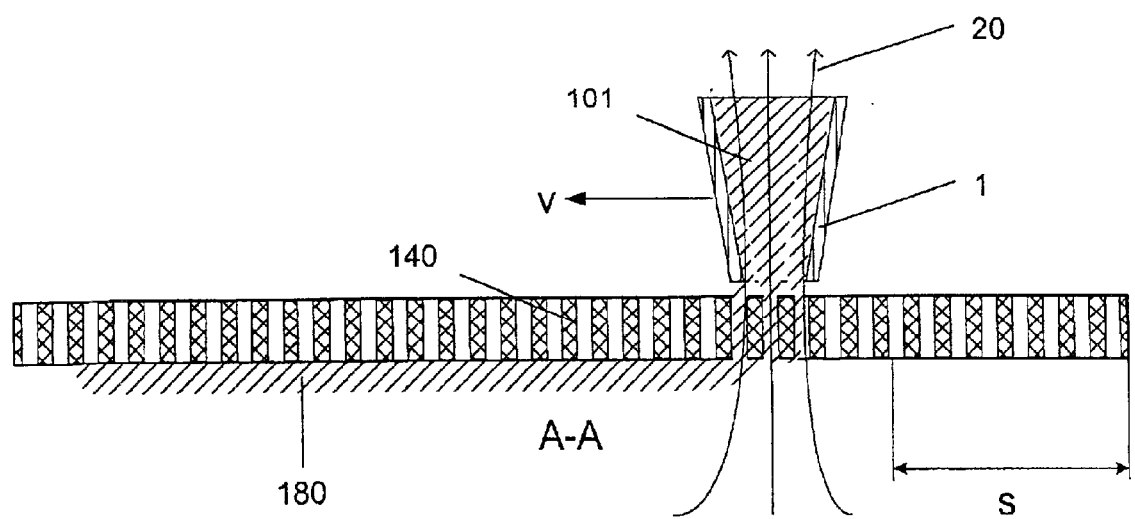
FIG. 19b illustrates in a sectional view an example of a dose on the surface of a perforated substrate member, showing the dose as it is being sucked from the surface of the substrate member by a moving nozzle adjacent to the opposite side of the substrate member as the dose.

Yet another embodiment of the powder Air-razor method is illustrated in FIG. 19a similar to FIG. 18a but with the powder dose 180 deposited on the underside of the substrate and a nozzle 1, adjacent to the upper opposite side of the substrate member 140 as the dose, in a starting position before the powder is released. FIG. 19b illustrates the powder Air-razor method by showing the powder as it is being released, de-aggregated and dispersed from the surface of the substrate member 140 by a stream of air, mainly going through the powder then the perforations and into the moving nozzle, on the opposite side of the substrate member as the dose.

Figure 20A:
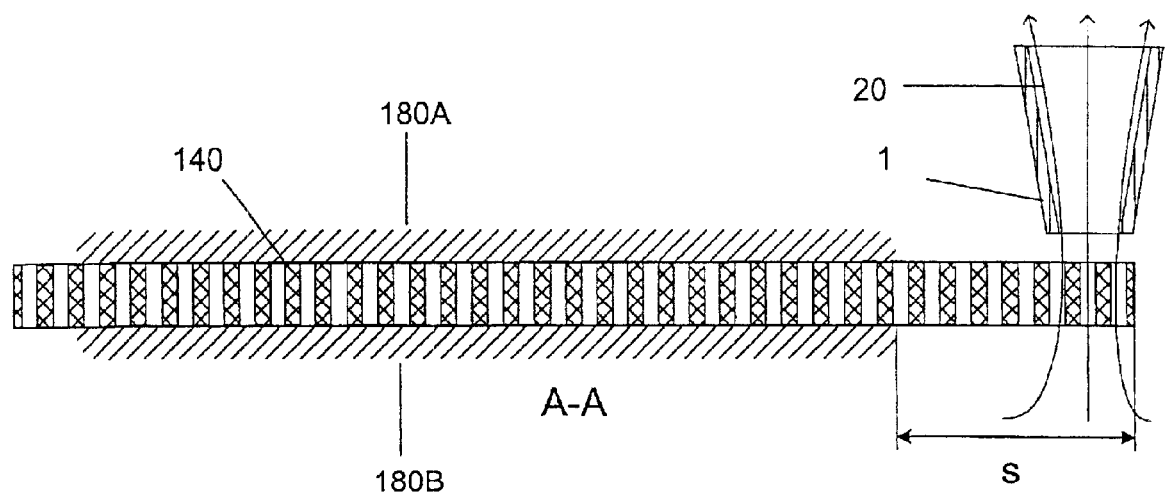
FIG. 20a illustrates in a sectional view an example of a metered dose formed as two part-doses, one on each side of a perforated substrate member and a nozzle adjacent to a first side of the substrate member in a starting position before the dose is released.
Figure 20B:
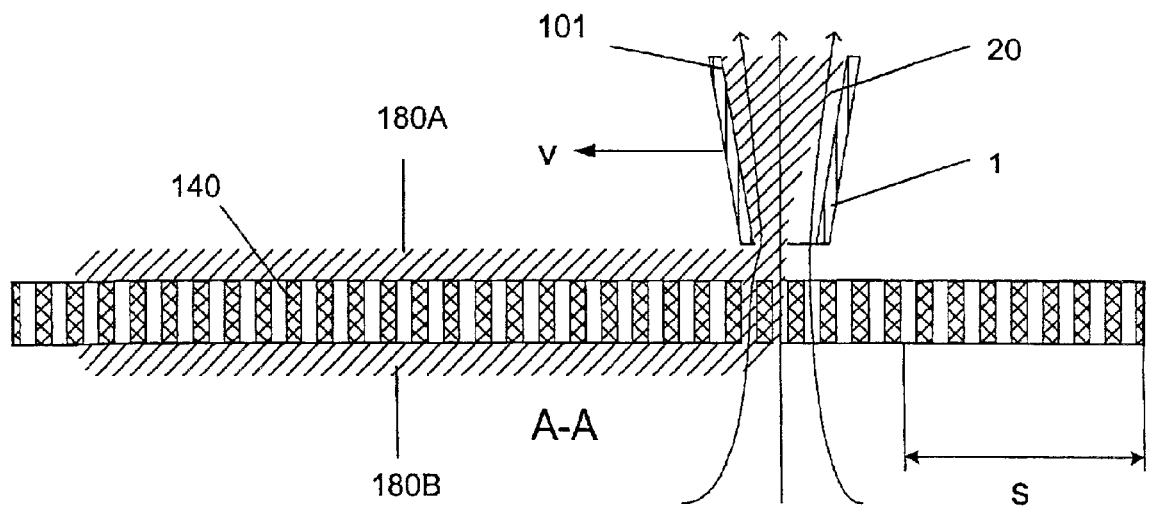
FIG. 20b illustrates in a sectional view an example of a metered dose formed as two part-doses, one on each side of a perforated substrate member and a moving nozzle adjacent to a first side of the substrate member sucking up the powder particles off both sides dispersed into the air stream.

Yet another embodiment of the powder Air-razor method is illustrated in FIG. 20a similar to FIGS. 18a and 19a showing medication powder deposited as two part-doses 180A and 180B onto both sides of a perforated substrate member 140. A nozzle 1 at side 180A is in a starting position before the powder is released. FIG. 20b illustrates a stream of air accessing the powder on the side 180B, then going through the perforations and accessing the powder on the side 180A before going into the nozzle, in a relative motion.

Figure 21:
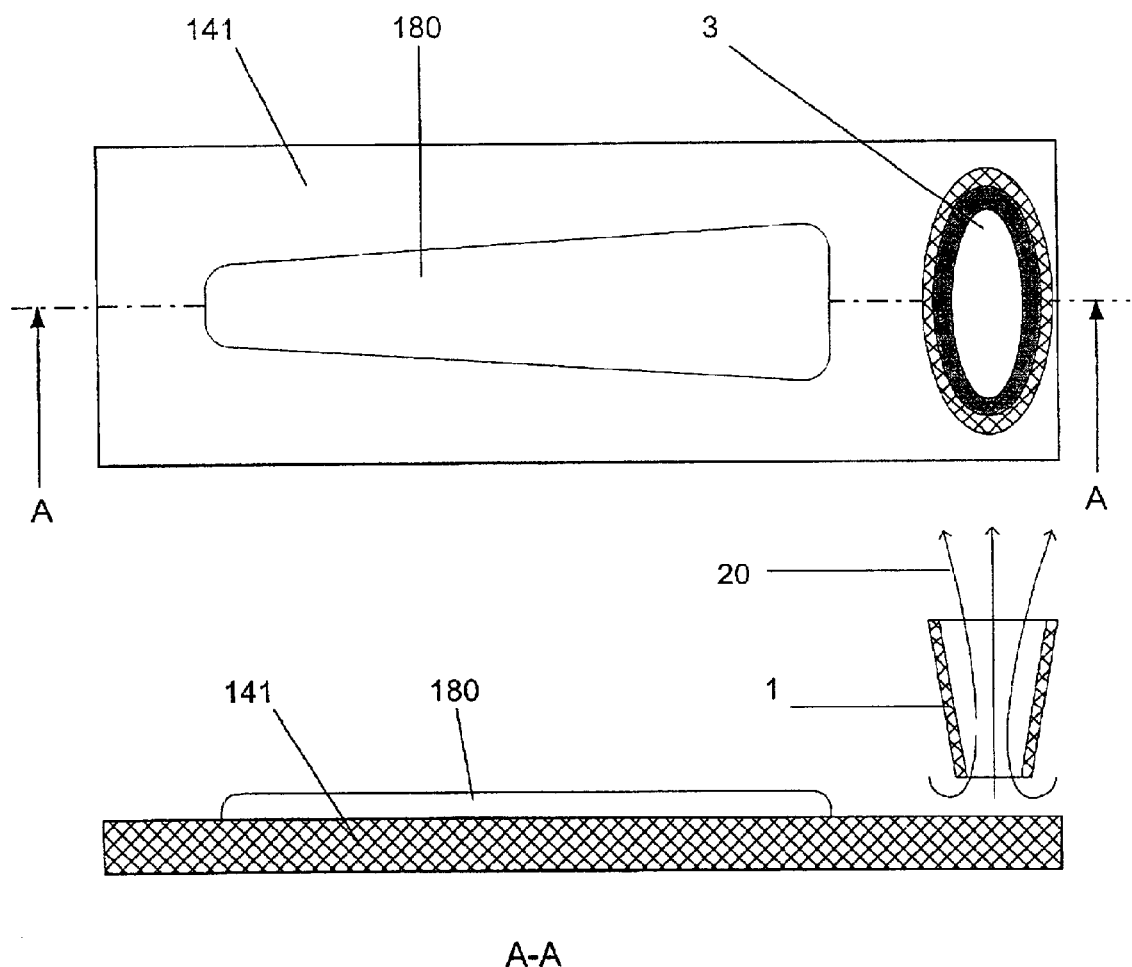
FIG. 21 illustrates a non-porous, non-perforated substrate member with a powder dose onto it and a nozzle with an elliptical inlet aperture adjacent to the same side of the substrate as the dose.
Figure 22:
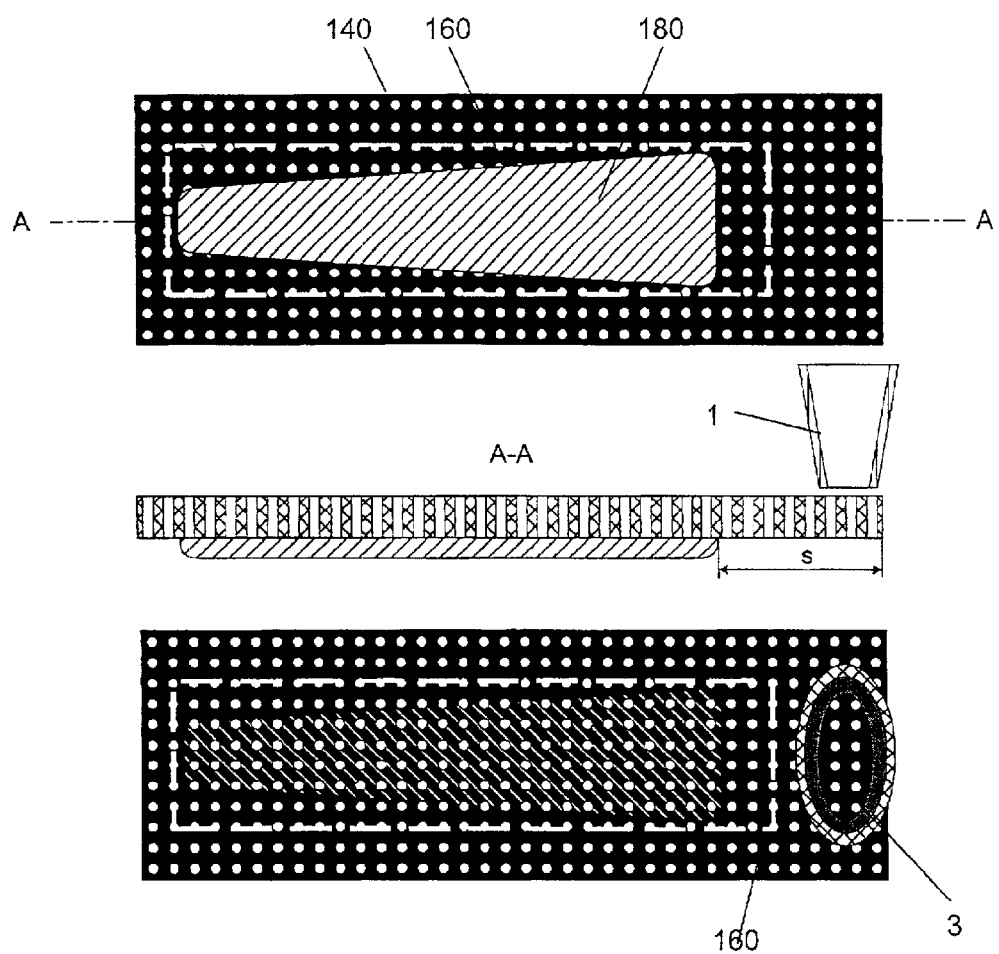
FIG. 22 illustrates a perforated substrate member with a powder dose onto it and a nozzle with an elliptical inlet aperture adjacent to the other side of the substrate as the dose.

FIGS. 21 and 22 illustrate in a top and a side view a substrate member 141 and 140 respectively with a load of powder 180 onto it and a nozzle 1 with an elliptical inlet aperture 3 and in a sectional view A—A the substrate member, powder dose and nozzle before the nozzle 1 has begun its relative motion in the direction of the powder 180.

Figure 23:
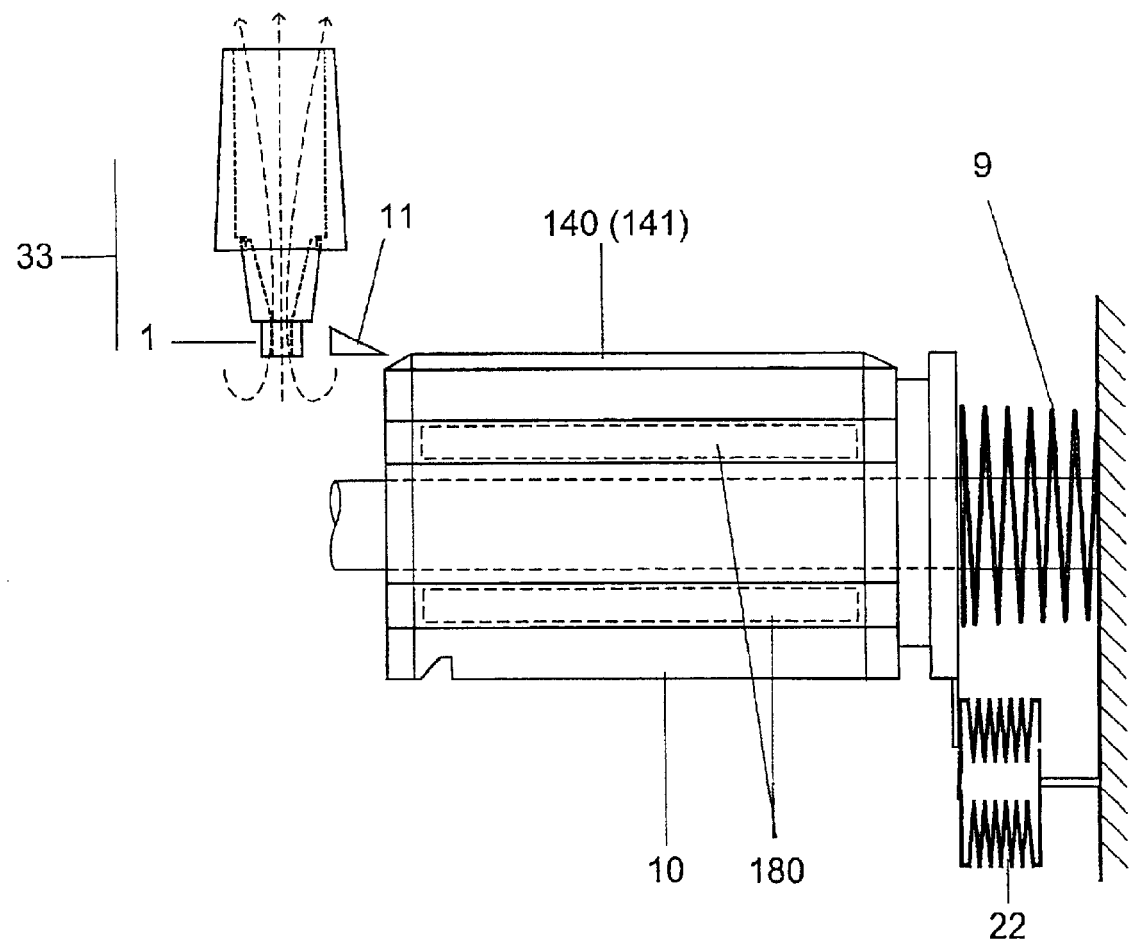
FIG. 23 illustrates an embodiment of a nozzle and a dosing member in a loaded state before release.
Figure 25:
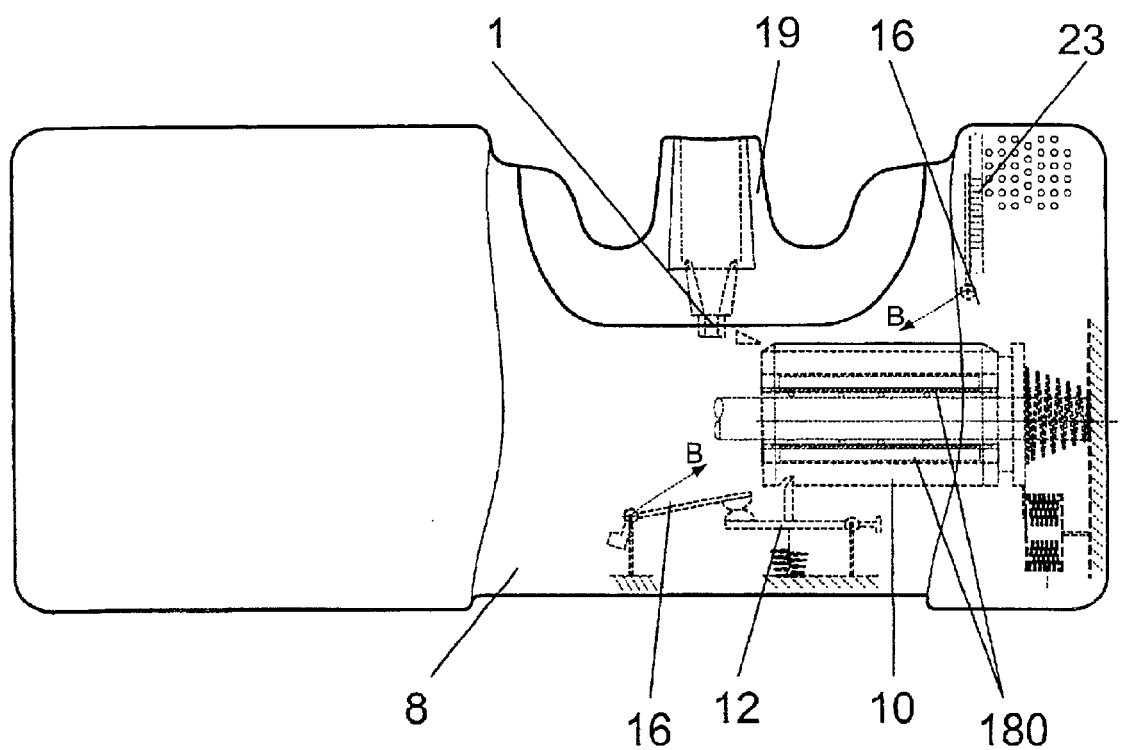
FIG. 25 illustrates an embodiment of an inhaler designed to apply a powder air-razor method.
Figure 26:
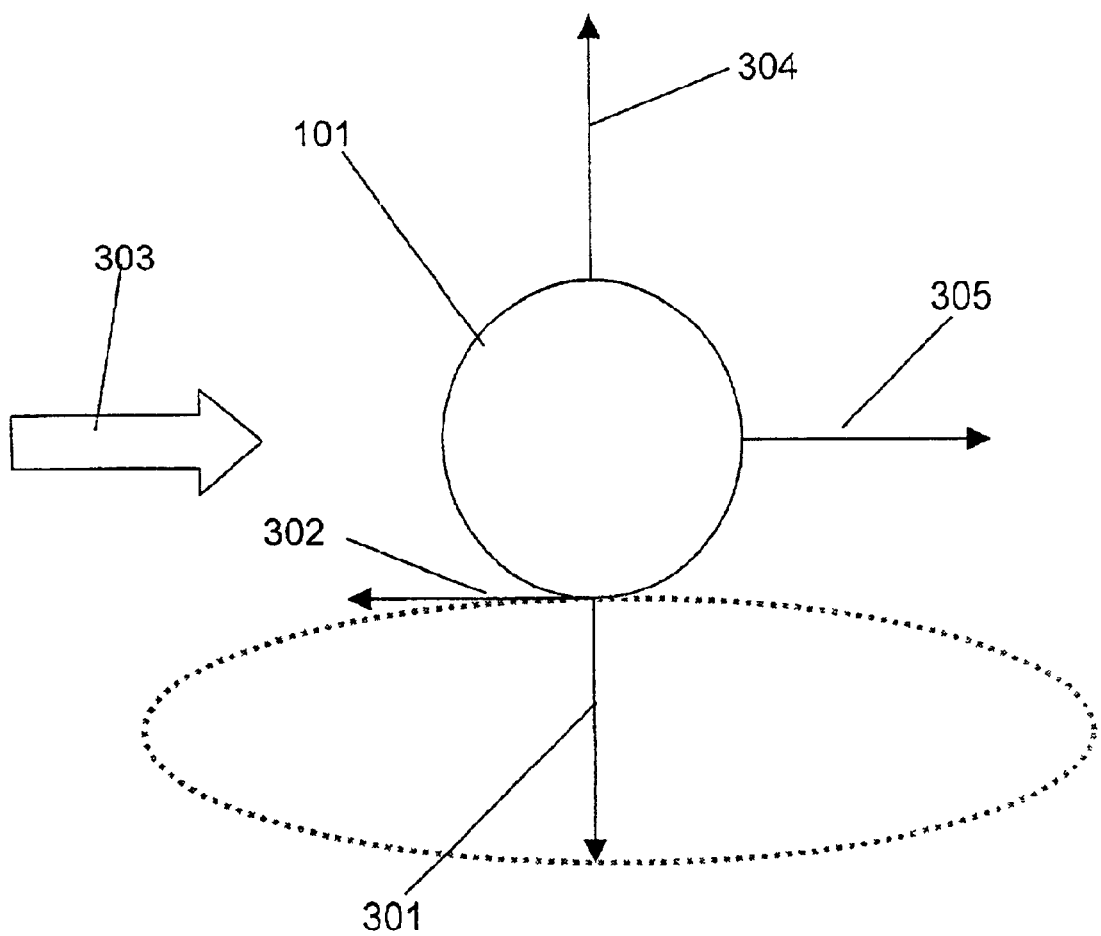
FIG. 26 illustrates the different forces acting on a stationary particle situated in a stream of air.
Figure 27:
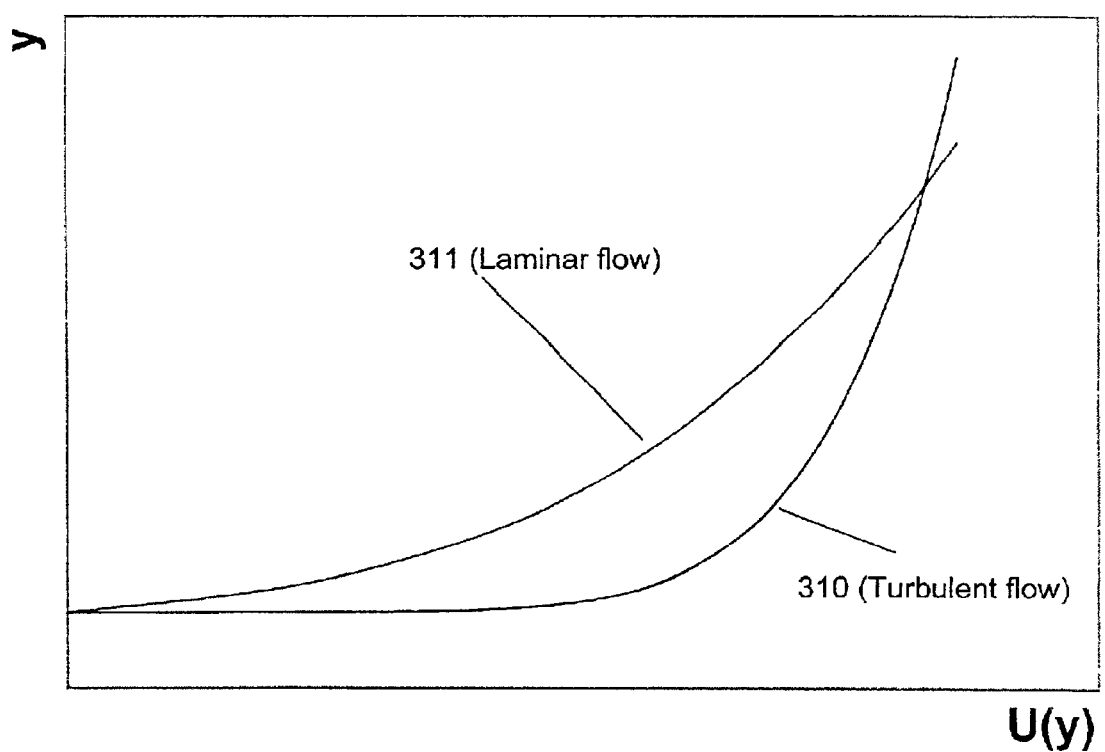
FIG. 27 illustrates fluid velocity as a function of distance to an object for laminar and turbulent flows.

FIG. 23 illustrates an embodiment of a powder Air-razor method in an inhaler context, showing a dosing member 10 comprising six substrate members 140 or 141 each provided with a metered dose of powder 180. A nozzle 1, part of a suction tube 33 and a dosing member 10 with one of the substrate members 140 or 141, are in positions for releasing an amount of powder. When a spring 9 releases (release mechanism not shown here but is indicated in FIG. 25) the dosing member 10, it is put in motion bringing the substrate member 140 or 141 and including the powder 180 past the nozzle 1. An airbrake 22 controls the speed of the dosing member and thereby the release interval of the powder 180, which is gradually sucked up by an air stream 20 going into the nozzle 1 because of suction applied to the suction tube 33. A foil cutter 11 may optionally be positioned in front of the nozzle, such that if the dose is protected by a foil, this will be first cut open and folded away to give the nozzle full access to the powder.

Figure 24:
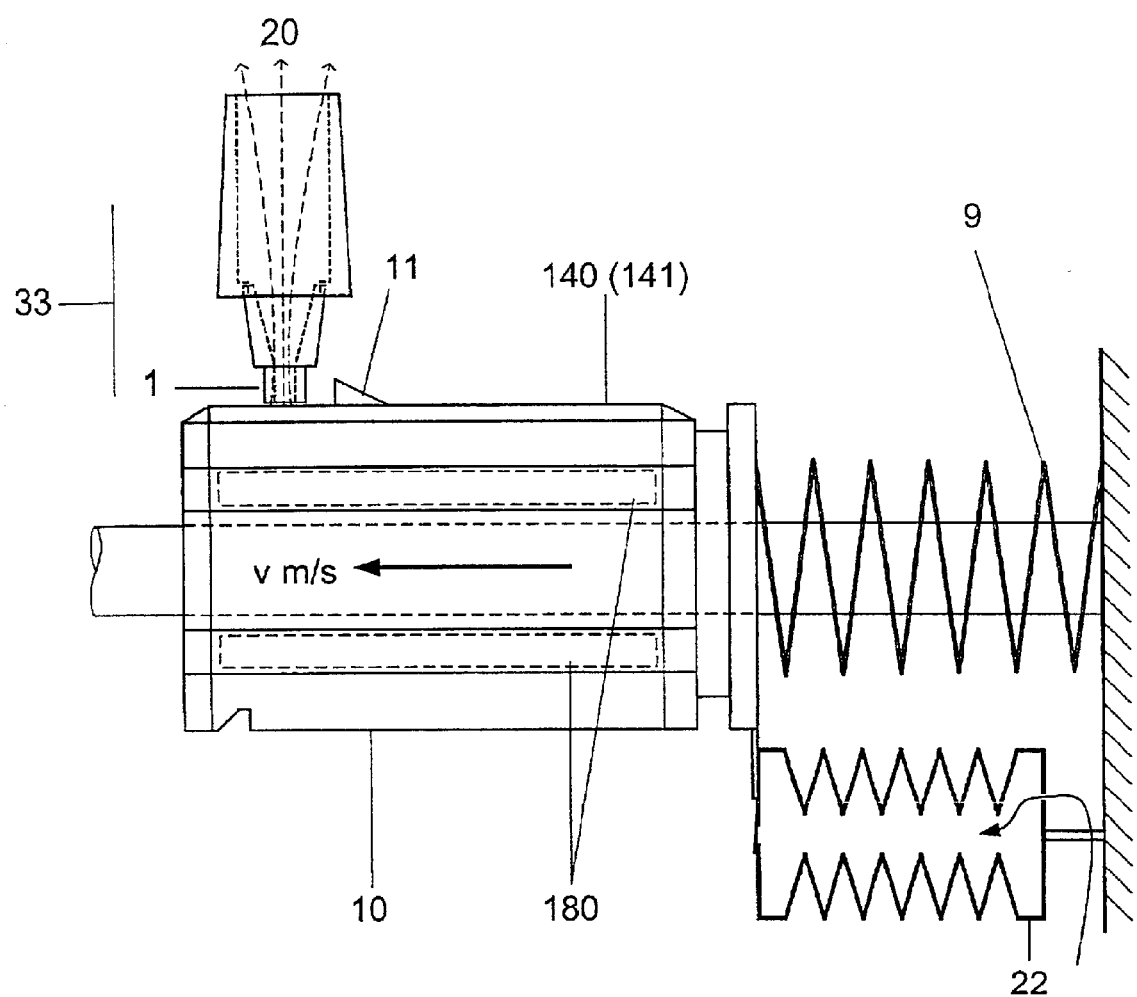
FIG. 24 illustrates an embodiment of a powder Air-razor method showing a nozzle and a dosing member in relative motion to each other in the process of releasing the powder dose.

FIG. 24 illustrates the powder Air-razor method in action, i.e. how the powder 180, deposited onto one of the substrate members 140 or 141, is gradually accessed by the nozzle 1 and the air stream as the dosing member and the suction tube 33 are put in a relative motion to each other.

FIG. 25 illustrates an embodiment of a powder Air-razor method applied in an inhaler 8 with a dosing member 10 comprising one or more substrate members 140 or 141 each provided with a metered dose of powder 180 to be administered sequentially to a user. A breath-actuation mechanism 16, lets air in and releases a catch 12 holding the dosing member (the loading and the complete releasing mechanisms are not shown) when the suction applied to a mouthpiece 19, in fluid connection with the suction tube 33, is sufficiently strong.

A dosing member 10 may be executed in many different ways to suit different types of inhalers. A dosing member may carry one or more doses on substrate members 140, 141 as described in our Swedish Patent No. SE 504 458 C2, which is hereby included by way of reference. In all cases, suitable substrate members may be selected from electrically conducting, dissipative or insulating materials or combinations of different such materials to give optimum inhalation performance of a metered dose 180 of a particular drug. The selection of a suitable substrate member material is also dependent on the chosen method of depositing a medicament dose. A substrate member is preferably a thin, flat sheet or film, less than 2 mm thick, with an area between 5 and 1000 mm$^2$ and having a target area for a dose in a range 0,5–1000 mm$^2$. A dose is intended to be formed within the dose target area 160, but the actual area occupied by the dose, termed dose area, may be less than 100% of the dose target area. The dose 180 is preferably spatially extended and formed as a strip of powder between 0,5 and 25 mm wide and between 1 and 500 mm long. The relative motion, illustrated in FIGS. 13–24, between the extended dose 180, i.e. the relevant substrate member 140 or 141, and the nozzle 1 must be arranged to follow the layout of the substrate on the dosing member. The contour of the extended dose is in turn defined by the type of inhaler from which the dose is supposed to be administered. Consequently, the contour of the dose may be e.g. linear, circular, spiral formed, a series of individual spots or some combination thereof.

Theoretical Background to the Concept of a Powder Air-razor Method

Adhesion of Particles

Particles adjacent to other particles or to a substrate member will adhere to each other. Many different types of adhesive forces will play roles in the total adhesive force between a particle and the environment, whether another particle, an aggregate of particles, a substrate member or a combination thereof. The types of adhesive forces acting on a particle can be van der Waal forces, capillary forces, electrical forces, electrostatic forces, etc. The relative strengths and ranges of these forces vary with e.g. material, environment, size and shape of the particle. The sum of all these forces acting on a particle is hereinafter referred to as an adhesive force.

De-Aggregation and Entrainment of Particles

The main objective of the Air-razor method is to de-aggregate and entrain the deposited particles into the air stream. The particles may be loaded onto a substrate member in many layers in such a way that some particles are in contact with the substrate member whilst others are in contact only with other particles. A complete de-aggregation is to separate all the particles from each other. To separate a particle from its environment involves overcoming the adhesive force as well as the friction force, acting on the particle.

FIG. 26 illustrates forces acting on a particle. The force caused by airflow 303 acting on a particle 101 can be divided into two parts, drag force 305 acting parallel to the airflow, and lift force 304 acting perpendicular to the airflow. The condition for freeing the particle is in the static case that lift and drag forces exceed adhesion 301 and friction 302 forces.

In order to completely, or almost completely, de-aggregate particles it is not sufficient to let a force act on the particles with enough strength for release and entrainment. If a strong force acts on an aggregate of particles, such that more or less the same force acts on all particles, the aggregate will be entrained into the airflow without de-aggregating. The condition for de-aggregation may thus be stated as: The difference in external forces acting on two particles must overcome the adhesion and friction forces holding them together. Attaining a difference in force from airflow may be done efficiently by creating shear forces, and hence the Air-razor method makes use of high shear forces in the area of the powder deposited for instance onto a substrate member.

Shear Forces

Creating high shear forces implies creating a big velocity gradient in the flow, which is illustrated by the equation for shear stress in a fluid;

$$\tau = \mu \frac{dU(y)}{dy};$$

where $\mu$=Dynamic viscosity

U(y)=Air speed U is a function of y y=Distance from wall surface dU/dy=Velocity change per unit distance To develop high shear stress and thereby high shear forces on the particles, the main principles used by the Air-razor method are:

High velocity of the air stream

Use of flow streamlines close to a wall

Use of turbulent flow (side effect from high velocity)

High Velocity Flow

High velocity flow is the basis for high shear forces (close to a wall), drag forces, lift forces and turbulence. For a given pressure drop driving airflow, the objective should be to reach maximum velocity. The theoretical maximum velocity from a certain static pressure drop can be derived from Bernoulli's streamline theorem. In reality, there will always be dissipation of energy and the velocity will not reach the levels stated by the equation, but it can be used as a limit value.

$$p + \frac{1}{2}\rho u^2 = H;$$

where p=Static pressure

ρ=Density of fluid u=Velocity

H=Constant

The equation is called Bernoulli's streamline theorem. H is a constant along a streamline for an 'ideal' fluid. Hydrostatic pressure is here excluded from the equation.

The efficiency of the Air-razor method may be optimized by careful design of the geometry of involved flow elements with the aim to reach as high a velocity as possible in the de-aggregation area, but at the same time a smooth transportation of air in other areas. This will minimise the dissipative losses where not wanted and so preserve energy for use in the area adjacent to the powder. When suction is applied to a nozzle, a low-pressure develops that accelerates the air through the nozzle during a short period before a steady state condition is reached. Initially, during the start-up period as the air picks up inertia, the velocity is not high enough to generate the necessary shear forces. Preferably, during this initial period the airflow is allowed to build up before the powder onto a substrate member is brought adjacent to the nozzle. This ensures that the conditions for an efficient de-aggregation of the powder exist before a point on the border of the powder contour is attacked by the air stream.

Flow Close to a Wall

A high velocity flow close to a wall will create high shear forces and this is used in the present invention. The flow at zero distance from a wall is always zero. This is known as the 'No slip' condition and is true for all fluids. In a thin layer close to the wall the flow velocity will increase rapidly with the distance from the wall, and the shear stress in this boundary layer will be correspondingly high. This boundary layer can be laminar or turbulent. The velocity profile and gradient differ between turbulent and laminar boundary layers, where the higher gradients and thus shear stress exist in the turbulent layer. The Air-razor invention makes use of the concentrated flow close to the nozzle inside wall as well as the wall of the substrate member, and especially the small gap between the aperture wall on the nozzle inlet and the substrate member.

The area experiencing high shear stress is normally small in relation to the area occupied by the powder. Therefore, a relative motion between the nozzle and the powder is introduced. This allows the concentrated small area of high shear stress to traverse the entire amount of powder for instance onto a substrate member.

Turbulent Flow

FIG. 27 illustrates in form of a diagram typical velocity characteristics for laminar 311 and turbulent 310 boundary layers. The velocity gradient and so the shear stress is larger in the turbulent layer. A turbulent flow, either in a boundary layer or in a free streaming flow, is characterized by irregular flow with eddies in various sizes and frequencies. Turbulent flow fluctuates in both time and space. In any particular moment, high gradients of velocity can be seen and so it is clear that high shear stress exists in the turbulent flow away from wall surfaces. This means that particle aggregates can be de-aggregated within a turbulent air stream even after the entrainment into air of an aggregate of particles. Another advantage of turbulence depends on the fluctuations in the turbulent flow with time, which will affect the particles with a force varying in time. In fully developed turbulence, the frequency of the fluctuations will cover a large span, i.e. from low to high frequencies. Should the frequency of the varying force come close to a resonance frequency of a particle-particle system or a particle-wall system, the amplitude will grow stronger and separation may occur even though the static force is too weak for separation.

The criteria determining whether the flow is turbulent or not are Reynolds number together with the geometry of the fluid transporting channel. The absolute level of Reynolds number where transition from laminar to turbulent flow will take place depends on the surface roughness and said geometry. Keeping these constant, the value of Reynolds number will determine the nature of the flow. As seen below Reynolds number is proportional to velocity, hence the velocity has a direct influence on the turbulence.

$$R_e = \frac{U_\infty L}{v};$$

where $R_e$=Reynolds number
$U_\infty$=The free stream velocity
L=Typical length
v=Kinematical viscosity Air-Razor Movement The importance of shear forces for an efficient de-aggregation of particles and the theoretical background as to why has been discussed in the foregoing. The relative motion introduced between the nozzle and the load of powder, i.e. the substrate member normally serving as carrier, is instrumental in attaining and maintaining the desired conditions stated for de-aggregating all of a powder dose and not just part of it. The main advantages given by the motion are:

During an initial acceleration phase inertia builds up giving a high velocity airflow Shear forces close to a wall are spread over a large area over time Efficient use of energy Inertia Build Up The low-pressure created by the suction through the nozzle drives air to flow in the direction of the low-pressure. Building up inertia means accelerating the mass in a system, i.e. the mass of the air itself, hence giving the desired high velocity airflow after the acceleration period. The velocity of the flow increases to a point where the flow resistance makes further increase impossible, unless the level of low-pressure is decreased, i.e. the pressure drop is increased, or the flow resistance is decreased.

Shear Force Spreading

The area for de-aggregation with high shear forces is concentrated close to the wall of the nozzle. This concentrated area is small compared to the dose area onto a substrate member, especially if the dose comprises finely divided powder of high porosity. The relative motion introduced between the nozzle and the dose will make the small and concentrated area of high shear stress traverse over the area occupied by the dose. Depending on the actual spatial distribution of the powder in the extended dose and the distance perpendicular to the direction of the motion between the powder and the nozzle inlet aperture, it may occur that the nozzle makes contact with some of the powder. In such cases the efficiency of the Air-razor method is not detrimentally affected because of the "hoover" effect. The velocity of the airflow will not be affected by the motion of the nozzle in relation to the powder dose, because the speed of the relative motion is very much lower than the velocity of the airflow going into the nozzle inlet. However, the motion of the nozzle forcibly shifts the position of the driving low-pressure relative the contour of the dose in the direction of the motion. Thus, the area of high shear forces moves along a path, controlled by the relative motion of the nozzle, such that the high shear forces gradually disperse powder particles into air. Preferably, the path begins just outside a point of contact between the high shear force area of flowing air and the border of the powder dose contour and follows the contour outline from the beginning until the end. Thus, the gradual de-aggregation and dispersal of a medication powder is an inherent essential characteristic of an Air-razor method.

Figure 28:
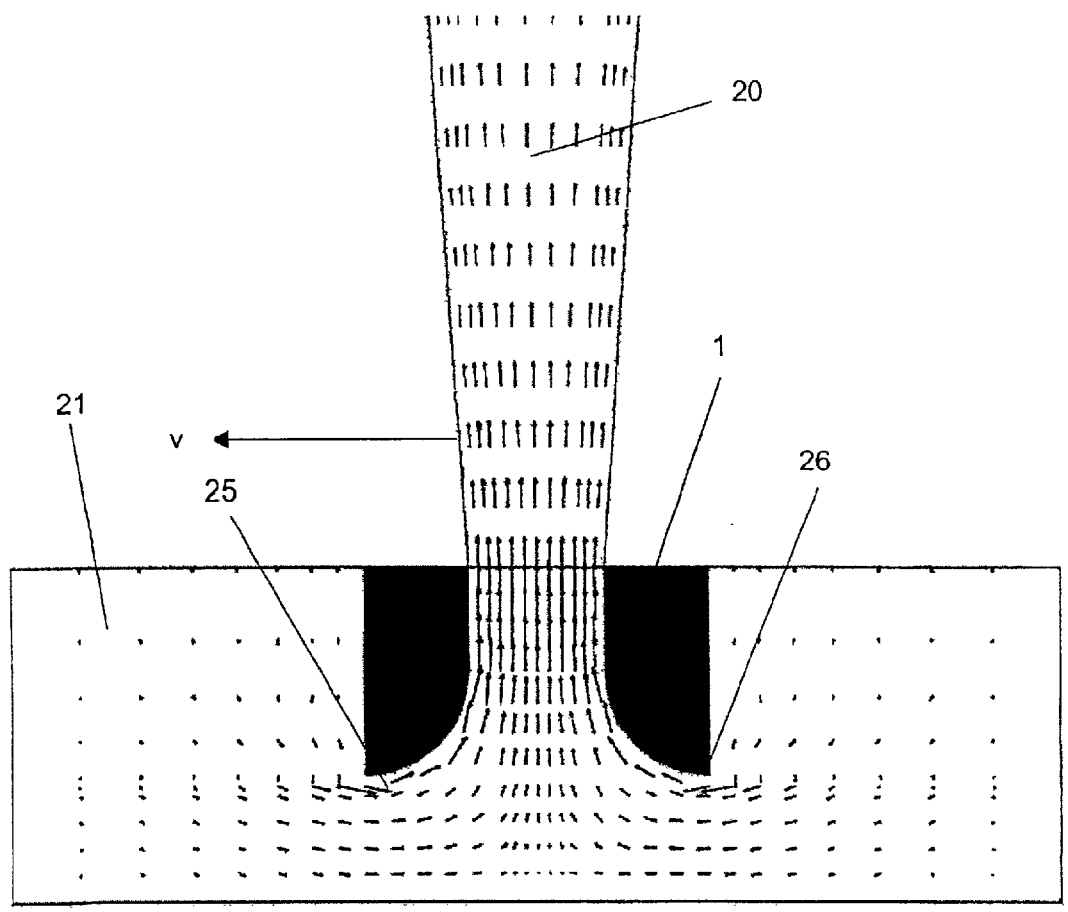
FIG. 28 illustrates an embodiment of a nozzle inlet opening and the air speed pattern developing during an applied suction effort.

The area of high shear stress adjacent to a nozzle is illustrated in FIG. 28. FIG. 28 illustrates graphically the resulting air speed from a suction effort applied to the nozzle outlet as a function of coordinates in a plane perpendicular to a substrate member plane through the longitudinal centerline of the same, thus showing half of a cross section view of the nozzle 1. The air velocity is illustrated by a multitude of arrows pointing in the direction of the flow, the length of the arrows indicating the relative velocity of air at the point in question, thus showing how the air velocity varies with the position relative the nozzle aperture. The direction of the relative motion between the nozzle and powder load is indicated by the arrow "v". Still air 21 is gradually accelerated into an air stream 20 of 60 1/min, steady state, going into the nozzle and controlled by the suction. The resulting shear forces reach a maximum in the area designated 25. The illustration in FIG. 28 is an example of an embodiment of a nozzle. The area of the nozzle aperture may have different shapes 3 (see FIGS. 21 and 22) for different applications, but a circular or elliptic shape is preferred. Likewise, the aperture wall thickness and curvature 26 may be given different forms depending on the application, since the form has a great influence on the flow pattern for the air being sucked into the nozzle.

Efficient Use of Energy

The dosing time interval for de-aggregation and dispersal of powder by an Air-razor method may be selected, depending on the application, within a time frame of an inhalation. Most prior art inhalers will use the inhalation power from the user during a short period only. This means that the total energy used for de-aggregation is correspondingly low in these inhalers, unless external de-aggregation energy is supplied. The time interval for an Air-razor delivery may e.g. be set to 1 second, which means that the inhalation power during this full second is used for de-aggregating particle aggregates.

$$E = \int_0^T P(t) \cdot dt$$

The total energy E equals the time integral of the power P over the entire period T, e.g. T=1 second.

Should the selected dosing time interval be too short, full entrainment of particles will not take place. The effect on a system using an Air-razor method will be large-scale retention of powder onto the substrate member. A model is therefore needed for assessing the number of particles dispersed into air with time. One such model assumes that a fluctuating turbulent flow is acting on the particles. Some of the eddies will be strong enough to separate particles in an aggregate or from a surface. The successful eddies will occur with typical time intervals based on probability. Each eddy will set a fraction of the total particles free. If all particles experience the same adhesion force, the model holds true and the entrainment rate would typically follow an exponential curve. However, the adhesion force varies from particle to particle and some will stick harder than others will and the fraction of hard-sticking particles will increase with time. This slows down the release rate. Hence, a modified model has been suggested, which describes the rate of particle release as a 1/t-curve, where t represents time and so the total number of particles n dispersed in the airflow will typically follow its integral, a $\log_e$ (t)-curve, illustrated in FIG. 28. The curve describes the entrainment over a 'long time'. A significant fraction of the powder will also be released within a short time (typically 10 ms). The graph underlines the importance of using a moderate speed v between the nozzle and the powder envelope. Too high speed will give insufficient time on 'each spot' and thus leave a significant amount of powder undispersed, still onto the substrate member. Too low speed will jeopardize the objective of delivering the load of powder within a specified dosing time interval.

The preferred embodiments use substrate members to serve as carriers onto which medicament powders may be deposited in extended structures presenting suitable properties in terms of occupied area, powder contour, particle size, mass, porosity, adhesion etc for de-aggregation and dispersal into air by applying the powder Air-razor method. Substrate members are convenient means for applying the Air-razor method onto powder doses, but other means exist, which should be obvious to a person skilled in the art. The degree of particle aggregation and dose porosity play an important role in achieving the best possible fine particle fraction and dispersal into air of the powder as it is forcibly entrained in air as a result of a release process. Finely divided medication powders with primary particle size below 10 $\mu$m are rarely free flowing, but to the contrary quite given to forming aggregates. Thus, finely divided powders that are less prone to forming aggregates and/or requiring less energy to break up formed aggregates are preferred in Air-razor applications. For example, ordered mixtures may be used to facilitate de-aggregation and dispersion into air of the active substances, which optionally may include pharmacologically acceptable excipients, used e.g. to dilute the active substance or, indeed, to improve one or more qualities of the active substance, such as bioavailability or electrostatic properties.

An example of a suitable powder for an Air-razor application is an electro-powder. Electro-powder is defined as a prepared dry powder medication substance with or without one or more excipients meeting a set of electrical specifications for optimum electrostatic dose forming properties. For further details, see our Swedish Patent No. SE 0002822-5, which is hereby incorporated herein by reference.

An example of a suitable dose of medication powder, formed onto a substrate member to be used in an Air-razor application, is an electro-dose. The term electro-dose, presented in our Swedish Patent No. SE 0003082-5, which is hereby incorporated herein by reference, refers to a dose of pre-metered medicament powder intended for use in a dry powder inhaler. The electro-dose is formed from an electro-powder comprising an active powder substance or a dry powder medicament formulation with or without one or more excipients, the electro-dose being formed onto a substrate member, which is part of a dosing member.

An example of a preferred method of forming a metered dose utilizes an electrostatic or electro-dynamic field deposition process or combinations thereof for depositing electrically charged particles of a medication powder onto a substrate member, such as an electrostatic chuck or a dosing member. The so formed electro-dose presents suitable properties in terms of occupied area, powder contour, particle size, mass, porosity, adhesion etc for easy de-aggregation and dispersal into air by the powder Air-razor method. However, in prior art other methods of forming a powder dose exist, which are suitable for an Air-razor application, e.g. mechanical, pneumatic or chemical methods. For example, doses may be produced by conventional volumetric or gravimetric metering methods, optionally followed by exposing the doses to a supply of energy. The purpose of supplying energy, e.g. by vibrating or giving the dose an energy impulse, would be to give the dose optimal spatial and porous qualities to be suitable for a powder Air-razor application.

In a preferred embodiment, exemplified in FIGS. 17a and 17b, the powder Air-razor method involves the introduction of a controlled relative motion between an extended dose of powder 180 deposited onto a substrate member 141 and a suitably arranged nozzle 1, which collects and directs a local high velocity stream of air 20. By pointing the nozzle inlet towards the powder contour onto the substrate element, the power of the air stream, resulting from the suction effort, de-aggregates and disperses into air the particles 101 of the accessed powder on the substrate member. As the nozzle moves in the direction of the extended contour of the deposited powder of the dose, primary particles and particle aggregates are gradually accessed and subjected to the shearing stresses and inertia power of the air stream going into the nozzle inlet aperture. Thus, the powder Air-razor method sequentially de-aggregates, releases, disperses and entrains individual particles into the air flowing into the nozzle.

In other embodiments of the powder Air-razor method, the substrate member may be replaced by other devices or arrangements for implementing the necessary relative motion of a medicament powder in relation to the nozzle. It is for instance possible to arrange a vibrating element or a gravitation feeder, or a screw feeder or a conveyor feeder or a pneumatic tube feeder and similar devices for moving powder gradually from a powder store to a position where the powder may be accessed by the air stream going into the nozzle, thus achieving the Air-razor effect. The nozzle may remain stationary or moving relative to other elements, participating in the process of de-aggregation and dispersal of powder into air, but still the result of the process depends on the relative motion between powder and nozzle. A consequence of the high efficiency of the powder Air-razor method is that a high proportion of available powder presented in advance of an inhalation is de-aggregated and dispersed into air, regardless of how the powder is presented i.e. if a substrate member serves as carrier for the powder or if powder is made available by other means. The accumulated mass of active medication particles in a dose that are dispersed into inhalation air by the Air-razor method, may be de-aggregated to at least 40% fine particle fraction (FPF) by mass based on the available active medication particles in the powder dose. Preferably, the Air-razor method may be capable of de-aggregating said powder mass to at least 50% FPF and more preferably to at least 60% FPF. The definition of FPF in this context is the fraction of delivered active medication particles by mass with a maximum aerodynamic particle size of 5 $\mu$m.

The first objective for the Air-razor method is to release individual fine particles into air i.e. to overcome the adhesive forces, such as van der Waal, electrostatic, gravity, friction etc, binding a particle to other particles in the aggregates of the powder and/or to the substrate surface. The second objective for the Air-razor method is to direct all airborne particles into the nozzle with as few lost particles as possible. The particles entering the nozzle should then be transported entrained in air to the airways of a user by means of a suitably arranged fluid channel. To fulfill the objectives a source of energy is required. Surprisingly, it has been found that the available drive power from the suction effort by the inhalation of a user provides ample energy for the powder Air-razor method. A normal inspiration effort by an adult user can be shown to produce a low-pressure approximately in a range 1–8 kPa. While a low-pressure in this range is usable, the preferred embodiment uses a range 1–4 kPa for ease of use by most people. Experiments have shown that the limited low-pressure, or drive pressure, thus produced may be used very efficiently, rendering external sources of power unnecessary in the inhalation process. Although the powder Air-razor method works equally well with an external power source, which partially or completely supplies suction power, an external power source does not offer any benefits and is therefore superfluous. However, the relative motion between powder and nozzle, necessary to make use of an Air-razor method, is preferably not powered by the inhalation effort, although this would be entirely possible. Instead, the relative motion may be arranged in many different ways, including e.g. mechanisms comprising spring elements with a capacity for storing potential energy given by the user in handling the inhaler device.

The conclusions for an Air-razor method are:
1. Make the nozzle inlet opening flow efficient, such that as little energy of the available inhalation pressure drop as possible is lost. Instead, the pressure drop should be used to produce airflow of highest possible speed into the nozzle, thereby optimizing the shear stress and turbulence acting on the particles.
2. Introduce a relative motion between the powder and the nozzle. The relative speed should be chosen depending on the application, e.g. dose area, dose size, type of patient etc, and not faster than making sure that all particles of the available powder are subjected to high air speeds, such that retention is kept low.

In line with the first conclusion, the present invention makes the use of baffles or other restrictions in the downstream flow path for creating turbulence, impaction and thereby de-aggregation superfluous, contrary to common solutions in prior art. The available energy for de-aggregation and dispersal is concentrated to areas around the nozzle inlet opening, leaving the interconnecting flow channels up to and including a mouthpiece with the single task of transporting the airborne particles to the user with a minimum of particle retention. By using the Air-razor method, retention in the downstream flow path may therefore become substantially reduced, thus presenting an opportunity for delivering a very high share of the available powder dose to the user and with an excellent FPF value.

In the context of the document, the term "adjacent to" is often used to describe the distance between the plane of a nozzle inlet opening and the plane of a surface of a substrate member or the top plane of the contour of a powder dose onto a surface of a substrate member. Normally these planes are parallel. For maximum Air-razor effect, it is advantageous if the distance from the nozzle inlet plane to the dose, which is going to be sucked up by the air stream into the nozzle, is shorter than a millimeter. The design objective of the inhaler where the Air-razor method is implemented, manufacturing tolerances and other factors will influence the decision where the nozzle should be positioned relative to the substrate member or the dose.

The teaching of the invention is unaffected by which mechanisms are deployed to bring about the relative motion between the members involved. Thus, it is immaterial for the present invention if the nozzle is the moving part and the substrate member is stationary or vice versa or if a combination of nozzle/substrate motions relative yet another fixed or moving element is used. In a preferred embodiment, see FIG. 21, the entrance aperture 3 of the nozzle 1 is shaped in an elliptical or slit-like fashion, such that the aperture is sufficiently wide to cover the width of the area occupied by powder 180 on the substrate 140. Relatively speaking, in a preferred embodiment the nozzle describes a motion from a start position to an end position, traversing across all of the occupied area of the dose in one stroke. Advantageously, the start position of the nozzle is outside the occupied area by a distance "s" (s≧0+size of aperture) to allow the suction-initiated airflow to build up through the nozzle to a point before the relative motion brings the nozzle adjacent to the powder. In such a preferred embodiment, the power and shearing stress of the powder Air-razor method is established before it approaches the border of the dose contour and begins to attack particle aggregates of the powder. A further improvement of the powder Air-razor method is the introduction of a suction related triggering of the flow into the nozzle, such that the resulting air speed is sufficiently high to generate the necessary powder Air-razor effect. In a preferred embodiment, the aperture of the nozzle is brought in close proximity to the substrate member and may even contact it, although not generally contact the load of powder onto the substrate member. Depending on the dose contour, e.g. if the dose is disturbed prior to the inhalation cycle, the nozzle may contact some of the powder in the dose during the delivery without any significant degradation of the Air-razor performance regarding de-aggregation and dispersal efficacy. In other embodiments, the relative motion between substrate member and nozzle may comprise more steps than one, which may be arranged in a discontinuous pattern. E.g. a pattern may be devised to let a nozzle with a smaller aperture cover the occupied area of the powder by traversing more than once across different parts of the powder area, covering a small area of the total aggregated area of the powder each time. The particles 101 thus cut free sequential and de-aggregated from the particle aggregates by the powder Air-razor method, are rapidly entrained in the air stream going into the nozzle.

In contrast, many prior art inhaler devices begin the powder release cycle by introducing the powder in the channel connecting the air inlet and the final mouthpiece air outlet. The powder is thus surrounded by a volume of stationary air. This considerable volume of air is then accelerated by the suction effort, normally provided by a user, sometimes boosted by added external energy, e.g. by vibrating the medicament powder or giving it an extra puff of pressurized air. All of the powder is subjected to this treatment at the same moment resulting in unsatisfactory de-aggregation of the total powder mass entrained in the air. In short, this means poor efficacy, because not all of the powder is subjected to the necessary shearing stress level for de-aggregation to really happen. Further, because the speed of air surrounding the powder is zero when the release process begins, some of the particle aggregates in the powder will be torn loose during the acceleration phase when the shearing stress of the airflow is not strong enough to de-aggregate the aggregates and accordingly they are delivered as intact aggregates. Within published specification limits, the present invention of a powder Air-razor discloses that all of the powder, which is accessed by the moving nozzle, is indeed subjected to the necessary shearing stress to be de-aggregated.

Interestingly, tests have shown that there are no distinct performance differences between a perforated substrate member 140 and a non-perforated substrate member 141 when used in an Air-razor application. In the case of a non-perforated substrate member, the nozzle must be positioned adjacent to the powder and at the same side of the substrate member as the powder, illustrated in FIGS. 17a and 17b. The air stream enters into the nozzle from the sides, to thereby cut particles 101 loose from the load of powder 180 in the process. On the other hand, if a perforated substrate member 140 is used, the de-aggregation and dispersal may be facilitated by air passing through the perforations and further through the load of powder 180 before the air stream 20 passes into the nozzle 1, see FIGS. 18a and 18b. A further improvement of the de-aggregation and dispersal may be attained from a perforated substrate member, if the nozzle may be positioned at the opposite side to the powder of the substrate member, such that the air stream hits the powder first before continuing through the perforations, and then into the nozzle inlet aperture, see FIGS. 19a and 19b. Theoretically, a perforated substrate member may offer better FPF results compared to a non-perforated substrate member, all other parameters being equal, because the shearing forces experienced by the powder on the perforated substrate member may be better distributed in the part of the powder where the airflow attacks at any given moment of the suction. The predominant airflow goes straight through the powder via the perforations or vice versa and into the nozzle rather than making a 90°–180° turn round the nozzle inlet periphery as in the case of the non-perforated substrate member. On average, a higher proportion of the powder is thus subjected to strong shearing forces, if the substrate member is perforated. In practice, however, what type of substrate member to use depends on the application, since the difference in performance for the Air-razor method applied to a non-perforated or perforated substrate member has been seen to be quite small.

Yet other embodiments of a perforated substrate member may position the nozzle on the same side of the substrate member as the medicament powder. Positioning the nozzle so that it may move close to the powder but preferably not in contact with it offers a possibility of forming e.g. a part-dose on both sides of the substrate member, as illustrated in FIGS. 20a and 20b. In such a case the two part-doses 180A and 180B will preferably be delivered in the same way as described above, only that the part-dose on the substrate member side opposite to the nozzle, termed 180B, will be sucked through the perforations to become mixed with the other dose, termed 180A. A possible application for forming part-doses on both sides of the substrate member may be in cases where two medicaments are incompatible to mix, but need to be administered at the same time to a user.

TEST EXAMPLES

In order to study the differences in fine particle fraction in the delivered dose to a user between a stationary nozzle and a moving one relative a dose during release of the dose, the following in vitro experiment was performed, using a finely divided lactose powder comprising 85% by mass of particles with a primary particle size less than 3 $\mu$m:

A. Stationary Nozzle and Perforated Substrate Member

A number of 30 spot-like doses of lactose, about 3 mm in diameter, with mass approximately 70 $\mu$g each were formed on a 150 mesh (150 stitches per inch) metal wire net serving as a substrate member. The substrate member was then positioned adjacent to a nozzle with its inlet at the opposite side of the substrate member to that of the dose. The area of the nozzle opening was somewhat larger than the dose. The nozzle outlet was connected to an Anderson impactor. The suction was then as quickly as possible brought up to a pressure drop of 2 kPa resulting in air speed 33.4 liters per minute. The dose was dispersed in the air stream going into the nozzle and delivered into the impactor. The release procedure was repeated for all 30 doses, total mass approximately 2 mg. The powder of the doses settled in the steps of the impactor. The particle distribution of the delivered mass in the various steps of the impactor is shown in Table 1. Retention in the nozzle connected to the impactor was determined to 54 $\mu$g. All masses were determined by a HPLC method.

The fine particle fraction, smaller than 5 $\mu$m, was determined by interpolation between steps 2 and 3 to 17.1% of the delivered mass and 16.7% of total determined mass.

TABLE 1

| Anderson Impactor | Flow-corrected particle cut-off size $\mu$m | Measured mass by HPLC $\mu$g | Distribution in each step of impactor % | Cumulative distributing in impactor % |
|---|---|---|---|---|
| Preimpactor |  | 1337 | 66.9 | 100 |
| Step 0 | 9.20 | 139 | 6.9 | 33 |
| Step 1 | 8.28 | 144 | 7.2 | 26 |
| Step 2 | 5.34 | 123 | 6.1 | 19 |
| Step 3 | 4.33 | 132 | 6.6 | 13 |
| Step 4 | 3.04 | 37 | 1.8 | 6 |
| Step 5 | 1.93 | 10 | 0.5 | 4.5 |
| Step 6 | 1.01 | 4 | 0.2 | 4 |
| Step 7 | 0.64 | 4 | 0.2 | 4 |
| Filter | 0.37 | 71 | 3.6 | 3.6 |
| Total |  | 2000 |  |  |

B. Air-Razor Method Applied to a Perforated Substrate Member

The arrangement was prepared such that 10 doses from the same batch of lactose as in A were formed as 15 mm long, 3 mm wide strips on the same type as in A of 150 mesh (150 stitches per inch) metal wire net serving as substrate members. The net was then positioned adjacent to the same nozzle as before with its inlet at the opposite side of the net to that of the dose, but some distance sideways removed from the area occupied by the dose. The diameter of the nozzle opening was somewhat larger than the dose width.

The nozzle was a part of the same measuring arrangement as before. The same Anderson impactor was used as before. The difference now was that the suction, 2 kPa, was applied first and the airflow was allowed to stabilize, before the net (in this case) was moved past the nozzle parallel to the dose strip, such that the dose was gradually sucked up by the flowing air going into the nozzle and delivered into the impactor. The release procedure was repeated for all 10 doses, total mass approximately 2.6 mg. The particle distribution of the delivered mass in the various steps of the impactor is shown in Table 2. Retention in the nozzle connected to the impactor was determined to 256 $\mu$g. The masses were determined by a HPLC method as before.

TABLE 2

| Anderson Impactor | Flow-corrected particle cut-off size $\mu$m | Measured mass by HPLC $\mu$g | Distribution in each step of impactor % | Cumulative distribution in impactor % |
|---|---|---|---|---|
| Preimpactor | — | 432 | 16.6 | 100.0 |
| Step 0 | 9.19 | 67 | 2.6 | 83.4 |
| Step 1 | 8.27 | 184 | 7.1 | 80.8 |
| Step 2 | 5.33 | 311 | 11.9 | 73.8 |

TABLE 2-continued

| Anderson Impactor | Flow-corrected particle cut-off size µm | Measured mass by HPLC µg | Distribution in each step of impactor % | Cumulative distribution in impactor % |
|---|---|---|---|---|
| Step 3 | 4.32 | 952 | 36.6 | 61.8 |
| Step 4 | 3.03 | 468 | 18.0 | 25.2 |
| Step 5 | 1.93 | 151 | 5.8 | 7.2 |
| Step 6 | 1.01 | 14 | 0.6 | 1.4 |
| Step 7 | 0.64 | 13 | 0.5 | 0.9 |
| Filter | 0.37 | 10 | 0.4 | 0.4 |
| Total | | 2602 | | |

The fine particle fraction, smaller than 5 µm, was determined by interpolation between steps 2 and 3 to 70.1% of the delivered mass and 63.8% of total determined mass.

C. Air-Razor Method Applied to a Non-Perforated Substrate Member

A sample was taken from a series of doses of lactose, of the same batch of lactose as in the earlier experiments A and B. Each dose was formed onto a non-perforated substrate member, the dose approximately a 15 mm long, 3 mm wide strip of powder. The selected sample dose was then positioned adjacent to the same nozzle with its inlet at the same side of the substrate member as the dose, but some distance sideways removed from the area occupied by the dose. The diameter of the nozzle opening was somewhat larger than the dose width.

The nozzle was a part of the same measuring arrangement as before. The same Anderson impactor was used as before. The suction, in this case 4 kPa, was applied first and the airflow was allowed to stabilize, before the substrate member (in this case) was moved past the nozzle parallel to the dose strip, such that the dose was gradually sucked up by the flowing air going into the nozzle and delivered into the impactor. The particle distribution of the delivered mass in the various steps of the impactor is shown in Table 3. Retention in the nozzle connected to the impactor was determined to 74.3 µg. The masses were determined by a HPLC method as before.

TABLE 3

| Anderson Impactor | Flow corrected particle cut-off size µm | Measured mass by HPLC µg | Distribution in each step of impactor % | Cumulative distribution in impactor % |
|---|---|---|---|---|
| Neck | — | 23 | 5.0 | 100.0 |
| Preimpactor | — | 12 | 2.6 | 95.0 |
| Step 0 | 8.33 | 12 | 2.5 | 92.4 |
| Step 1 | 7.50 | 31 | 6.7 | 89.9 |
| Step 2 | 4.83 | 72 | 15.7 | 83.1 |
| Step 3 | 3.91 | 136 | 29.6 | 67.4 |
| Step 4 | 2.75 | 78 | 17.0 | 37.8 |
| Step 5 | 1.75 | 28 | 6.2 | 20.8 |
| Step 6 | 0.92 | 10 | 2.3 | 14.6 |
| Step 7 | 0.58 | 9 | 2.0 | 12.3 |
| Filter | 0.33 | 47 | 10.3 | 10.3 |
| Total | | 459 | | |

The fine particle fraction, smaller than or equal to 5 µm, was determined by interpolation between steps 1 and 2 to 83.7% of the delivered mass and 72.0% of total determined mass. It is to be noted that the pressure in this case was 4 kPa compared to 2 kPa in the two earlier experiments. The results are therefore not directly comparable, but the test pressures are within the preferred range of 1–4 kPa.

The evidence of the experiments supports the claimed benefits for the inventive step of gradual de-aggregation and dispersal into air by introducing a relative motion between a nozzle and a dose of medication powder. Using the shearing stress near the nozzle inlet periphery and the impact of the streaming air to full potential onto a boundary part of the medication powder contour, achieve a very high degree of de-aggregation and high fine particle fraction in the particles dispersed into air. The relative motion between nozzle and powder means a gradual approach to the powder by the shearing forces making release of a considerable dose possible. The experiments show that the Air-razor method applied to a dose onto a non-perforated substrate member may give a very good performance, as does the Air-razor method applied to powder onto a perforated substrate member. By optimizing the adhesion force between particles and between particles and substrate in the deposited powder, by optimizing the powder area, by optimizing the nozzle geometry and by optimizing the speed of the relative motion between nozzle and powder, de-aggregation and fine particle fraction mass, smaller than or equal to 5 µm, is pushed very close to 100% of the mass of the available medication powder.

In a preferred embodiment the speed "v" of the relative displacement powder dose-nozzle in FIGS. 17b, 18b, 19b, 20b is controlled by suitable means, an element of which may be an air inlet valve, which opens when the pressure differential from the suction is suitably strong. Then, the resulting airflow quickly reaches the speed necessary for the powder Air-razor method to efficiently de-aggregate and disperse into air the particles of the dose. To minimize flow losses as much as possible the nozzle and the downstream connecting channel may be given a conical shape such that the outlet area is larger than the inlet area. Controlling "v" implicates that a most suitable dosing time interval may be defined during which delivery of a dose should take place. The dosing time interval depends on several factors, e.g. targeted area of the airways, nominal powder dose mass and type of user for the medication. From a starting point to an ending point the relative motion of dose versus nozzle must embrace the defined time interval, which normally is in a range of 0.01 to 5 seconds. The timing should be suitably selected for the application i.e. the points in time where the motion begins and ends within a time frame of a suction of air that is taking place.

It is therefore important to optimize the delivery of the dose by means of a new type of inhaler device, which takes full advantage of the powder Air-razor method. An embodiment of such a new inhaler device is disclosed in FIG. 25. Thus, the present method optimizes the delivery of the dose by taking full advantage of the described new powder Air-razor method and the qualities of an extended dose.

What is claimed is:

1. A method of de-aggregating and dispersing into air a dose of finely divided medication powder, releasably retained onto a substrate member, the dose intended for inhalation, comprising the steps of providing a nozzle comprising an inlet and an outlet and positioning a nozzle inlet aperture adjacent to or in contact with the substrate member;

applying a suction of air to the nozzle outlet, thus creating a local high velocity air stream flowing into the nozzle inlet aperture and out through the outlet;

introducing a relative motion between the nozzle and the substrate member and arranging the relative motion such that the nozzle inlet and the local, high velocity air stream going into the nozzle inlet aperture traverses the dose of finely divided medication powder, thereby producing a powder Air-razor effect in releasing and dispersing the powder dose;

de-aggregating particle aggregates within the dose of finely divided medication powder by utilizing the shearing stresses and inertia and turbulence of air in the local, high velocity air stream going into the nozzle inlet aperture, whereby the de-aggregated particles of the dose of finely divided medication powder are gradually dispersed into the air as available powder in the dose is gradually accessed by the air stream at a border of a dose area as the nozzle and dose are moved in relation to each other.

2. The method according to claim 1, comprising the further step of positioning the nozzle inlet in a start position outside the dose area, thus preventing disturbance and initial poor de-aggregation of powder of the dose before a suitable airflow into the nozzle inlet has had time to become established to create the powder Air-razor effect.

3. The method according to claim 1, comprising the further step of attaining at least 40% of the medication powder mass in the dose onto the substrate member to be dispersed as fine particles in the inhaled air stream leaving the nozzle, said fine particles having an aerodynamic diameter equal to or less than 5 $\mu$m.

4. The method according to claim 1, comprising the further step of
adjusting timing of the relative motion of the nozzle within a time frame of the suction of air taking place.

5. The method according to claim 1, comprising the further step of
selecting a time interval in a range 0.01 to 5 s for the relative motion of the nozzle from a start position to an end position within a time frame of the suction of air taking place.

6. The method according to claim 1, comprising the further steps of
arranging the substrate member to be electrically chargeable by induction, corona or tribo effect and capable of retaining such acquired charge after completing a charging procedure to be suitable for electrostatic or electrodynamic field deposition of finely divided medication powder in a dose forming process;
thus forming a medication powder dose, which, in connection with an inhalation, is to be de-aggregated and dispersed into air by means of the powder Air-razor effect.

7. The method according to claim 1, comprising the further steps of
arranging the substrate member, whether porous or perforated or neither, to be electrically neutral, not affecting particle adhesion forces electrically, by selecting the substrate member material or materials to be electrically isolating, dissipative or conducting or combinations thereof, thereby facilitating de-aggregation and dispersing into air of particles of a medication powder dose in connection with an inhalation by means of the powder Air-razor effect.

8. The method according to claim 1, comprising the further step of
depositing at least one finely divided medication powder onto a first or a second side or onto both sides of the substrate member.

9. The method according to claim 8, comprising the further step of
depositing finely divided medication powder onto a first and second side of the substrate member, said powder comprising optionally different medicament powders, a first medication powder onto the first side of the substrate member and a second medication powder onto the second side of the substrate member.

10. The method according to claim 8, comprising the further step of
selecting a porous or perforated substrate member, such that the nozzle, if positioned at the first side, can suck powder, if present, off the first side and powder, if present, on the second side off the second side through pores or perforations of the substrate member, such that powder from the first and the second side, if available, on either or both sides, will get sucked into the nozzle by the suction of air.

11. The method according to claim 1, comprising the further steps of
making a nozzle inlet area of the same order as or smaller than the dose area, and
arranging the relative motion of the nozzle such that the nozzle inlet covers at least the dose area in one or more traversing steps within a time frame during which the suction of air is taking place.

12. The method according to claim 1, comprising the further step of providing a usable pressure drop by the suction of a user in a range of 1–8 kPa and more preferably in a range 1–4 kPa.

13. The method according to claim 1, comprising the further step of defining a threshold value of vacuum from the suction necessary to trigger the flow of air into the nozzle, thereby ensuring that airflow is sufficiently high to generate the necessary powder air-razor effect.

14. A method of administering a dose of finely divided medication powder, releasably retained onto a substrate member, to a user inhaling through a dry powder inhaler, comprising the steps of
selecting a dry powder formulation of the medication powder in which at least one pharmacologically active substance provides a suitable aerodynamic particle size distribution for an intended medical application and site of action;
providing a nozzle comprising an inlet and an outlet and positioning a nozzle inlet aperture adjacent to or in contact with the substrate member;
applying a suction effort by a user to the nozzle outlet, thus creating a local high velocity air stream flowing into the nozzle inlet aperture and out through the outlet into the airways of the user;
introducing a relative motion between the nozzle and the substrate member and arranging the relative motion such that the nozzle inlet and the local, high velocity air stream going into the nozzle inlet aperture traverse the dose of finely divided medication powder, thereby producing a powder Air-razor effect in releasing and dispersing the powder dose into air just prior to it being inhaled;
delivering the dose of medication powder in de-aggregated form by utilizing the shearing stresses and inertia and turbulence of air in the local, high velocity air stream going into the nozzle inlet aperture, whereby the particle aggregates of the dose are gradually de-aggregated and dispersed into the inhaled air as available powder in the dose is gradually accessed by the air stream at a border of a dose area as the nozzle and dose are moved in relation to each other, whereby a delivered dose is composed of a majority, by mass, of fine particles.

15. The method according to claim 14, comprising the further step of positioning the nozzle inlet in a start position outside the dose area, thus preventing disturbance and initial poor de-aggregation of powder of the dose before a suitable airflow into the nozzle inlet has had time to become established to create the powder Air-razor effect.

16. The method according to claim 14, comprising the further step of attaining at least 40% of the medication powder mass in the dose onto the substrate member to be dispersed as fine particles in the inhaled air stream leaving the nozzle, said fine particles having an aerodynamic diameter equal to or less than 5 $\mu$m.

17. The method according to claim 14, comprising the further step of adjusting timing of the relative motion of the nozzle within a time frame of the suction of air taking place.

18. The method according to claim 14, comprising the further step of selecting a time interval in a range 0.01 to 5 s for the relative motion of the nozzle from a start position to an end position within a time frame of the suction of air taking place.

19. The method according to claim 14, comprising the further steps of arranging the substrate member to be electrically chargeable by induction, corona or tribo effect and capable of retaining such acquired charge after completing a charging procedure to be suitable for electrostatic or electrodynamic field deposition of finely divided medication powder in a dose forming process;

thus forming a medication powder dose, which, in connection with an inhalation, is to be de-aggregated and dispersed into air by means of the powder Air-razor effect.

20. The method according to claim 14, comprising the further steps of arranging the substrate member, whether porous or perforated or neither, to be electrically neutral, not affecting particle adhesion forces electrically, by selecting the substrate member material or materials to be electrically isolating, dissipative or conducting or combinations thereof, thereby facilitating de-aggregation and dispersing into air of particles of a medication powder dose in connection with an inhalation by means of the powder Air-razor effect.

21. The method according to claim 14, comprising the further step of depositing at least one finely divided medication powder onto a first or a second side or onto both sides of the substrate member.

22. The method according to claim 21, comprising the further step of depositing finely divided medication powder onto a first and second side of the substrate member, said powder comprising optionally different medicament powders, a first medication powder onto the first side of the substrate member and a second medication powder onto the second side of the substrate member.

23. The method according to claim 21, comprising the further step of selecting a porous or perforated substrate member, such that the nozzle, if positioned at the first side, can suck powder, if present, off the first side and powder, if present, on the second side off the second side through pores or perforations of the substrate member, such that powder from the first and the second side, if available, on either or both sides, will get sucked into the nozzle by the suction of air.

24. The method according to claim 14, comprising the further steps of making a nozzle inlet area of the same order as or smaller than the dose area, and arranging the relative motion of the nozzle such that the nozzle inlet covers at least the dose area in one or more traversing steps within a time frame during which the suction of air is taking place.

25. The method according to claim 14, comprising the further step of providing a usable pressure drop by the suction of a user in a range of 1–8 kPa and more preferably in a range 1–4 kPa.

26. The method according to claim 14, comprising the further step of defining a threshold value of vacuum from the suction necessary to trigger the flow of air into the nozzle, thereby ensuring that airflow is sufficiently high to generate the necessary powder air-razor effect.

* * * * *